US012765574B2

(12) United States Patent
Guerard et al.

(10) Patent No.: US 12,765,574 B2
(45) Date of Patent: Oct. 20, 2026

(54) PROTEIN HYDROLYSATE DERIVED FROM BLUE-BACKED FISH

(71) Applicants: SPECIALITES PET FOOD, Elven (FR); UNIVERSITE DE BORDEAUX, Bordeaux (FR); UNIVERSITÉ DE BRETAGNE OCCIDENTALE, Brest (FR); CENTRE NATIONAL DE LA RECHERCHE SCIENTIFIQUE (CNRS), Paris (FR); INSTITUT DE RECHERCHE POUR LE DEVELOPPEMENT (IRD), Marseilles (FR); INSTITUT POLYTECHNIQUE DE BORDEAUX, Talence (FR); ABYSS INGREDIENTS, Caudan (FR); INSTITUT FRANCAIS DE RECHERCHE POUR L'EXPLOITATION DE LA MER—IFREMER, Plouzane (FR); INSTITUT NATIONAL DE LA RECHERCHE POUR L'AGRICULTURE, L'ALIMENTATION ET L'ENVIRONNEMENT, Paris (FR)

(72) Inventors: Fabienne Guerard, Concarneau (FR); Cloé Oroy, Saint-Marcel (FR); Anne Lepoudere, Guer (FR); Mathilde Chataigner, Quincampoix (FR); Patrick Allaume, Caudan (FR); Anne-Laure Dinel, Merignac (FR); Corinne Joffre, Pessac (FR); Véronique Pallet, Pessac (FR); Fabienne Le Grand, Guilers (FR)

(73) Assignees: SPECIALITES PET FOOD, Elven (FR); UNIVERSITE DE BORDEAUX, Bordeaux (FR); UNIVERSITE DE BRETAGNE OCCIDENTALE, Brest (FR); CENTRE NATIONAL DE LA RECHERCHE SCIENTIFIQUE (CNRS), Paris (FR); INSTITUT DE RECHERCHE POUR LE DEVELOPPEMENT (IRD), Marseilles (FR); INSTITUT POLYTECHNIQUE DE BORDEAUX, Talence (FR); ABYSS INGREDIENTS, Caudan (FR); INSTITUT FRANCAIS DE RECHERCHE POUR L'EXPLOITATION DE LA MER—IFREMER, Plouzane (FR); INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 1118 days.

(21) Appl. No.: 17/632,198

(22) PCT Filed: Jul. 31, 2020

(86) PCT No.: PCT/EP2020/071717
§ 371 (c)(1),
(2) Date: Feb. 1, 2022

(87) PCT Pub. No.: WO2021/019093
PCT Pub. Date: Feb. 4, 2021

(65) Prior Publication Data

US 2022/0279814 A1 Sep. 8, 2022

(30) Foreign Application Priority Data

Aug. 1, 2019 (FR) ....................................... 1908837

(51) Int. Cl.
*A23J 1/04* (2006.01)
*A23J 3/04* (2006.01)
(Continued)

(52) U.S. Cl.
CPC . *A23J 1/04* (2013.01); *A23J 3/04* (2013.01); *A23J 3/341* (2013.01); *A23K 20/147* (2016.05);
(Continued)

(58) Field of Classification Search
CPC ...... A23J 1/04; A23J 3/04; A23J 3/341; A23L 33/12; A23L 33/18; A23L 33/115
See application file for complete search history.

(56) References Cited

U.S. PATENT DOCUMENTS

2008/0070870 A1 3/2008 Bruheim et al.
2019/0015433 A1 * 1/2019 Hallaraker ........... A61K 31/683
2019/0037882 A1 2/2019 Framroze et al.

FOREIGN PATENT DOCUMENTS

EP 2316426 A1 5/2011
FR 2835703 8/2003

(Continued)

OTHER PUBLICATIONS

International Search Report issued in International Application No. PCT/EP2020/071717; 8 pgs.

*Primary Examiner* — Katherine D Leblanc
(74) *Attorney, Agent, or Firm* — Maier & Maier, PLLC

(57) ABSTRACT

A protein hydrolysate obtained from at least one protein source from bluefish having (i) a degree of hydrolysis (DH) of at least 10%, (ii) at least 80% water-soluble protein with a molecular weight of less than 1000 Da, (iii) at least 0.3% phospholipids, and (iv) at least 0.5% DHA and EPA.

16 Claims, 19 Drawing Sheets

(51) Int. Cl.

| | |
|---|---|
| ***A23J 3/34*** | (2006.01) |
| ***A23K 20/147*** | (2016.01) |
| ***A23K 50/40*** | (2016.01) |
| ***A23L 33/115*** | (2016.01) |
| ***A23L 33/12*** | (2016.01) |
| ***A23L 33/18*** | (2016.01) |
| ***A61K 31/202*** | (2006.01) |
| ***A61K 35/60*** | (2006.01) |
| ***A61K 38/01*** | (2006.01) |

(52) U.S. Cl.
CPC ............ *A23K 50/40* (2016.05); *A23L 33/115* (2016.08); *A23L 33/12* (2016.08); *A23L 33/18* (2016.08); *A61K 31/202* (2013.01); *A61K 35/60* (2013.01); *A61K 38/012* (2013.01)

(56) References Cited

FOREIGN PATENT DOCUMENTS

| | | |
|---|---|---|
| FR | 2927336 | 8/2009 |
| FR | 2966016 | 4/2012 |
| FR | 3036923 | 12/2016 |

* cited by examiner

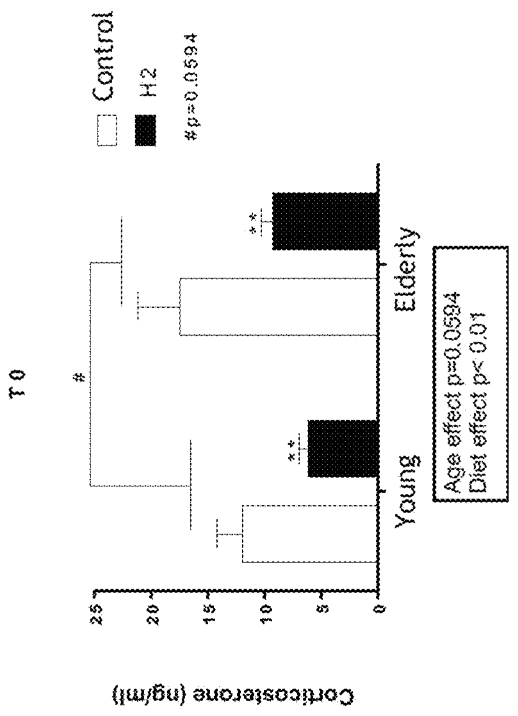
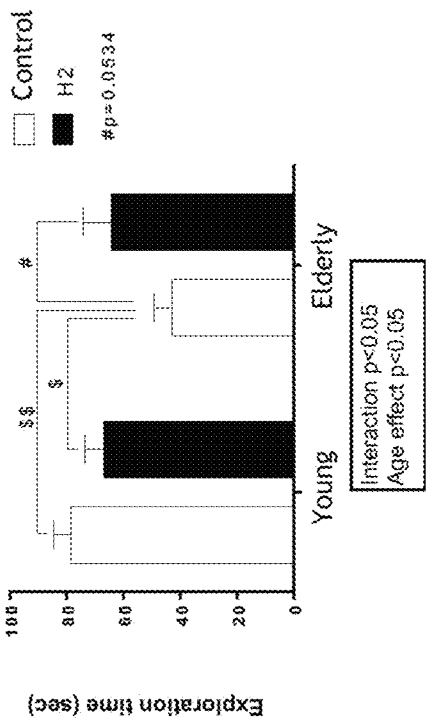
Fig. 4

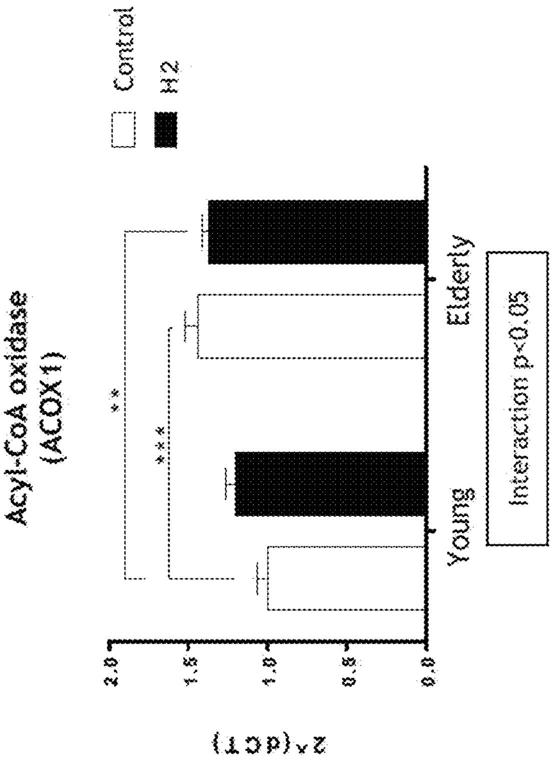
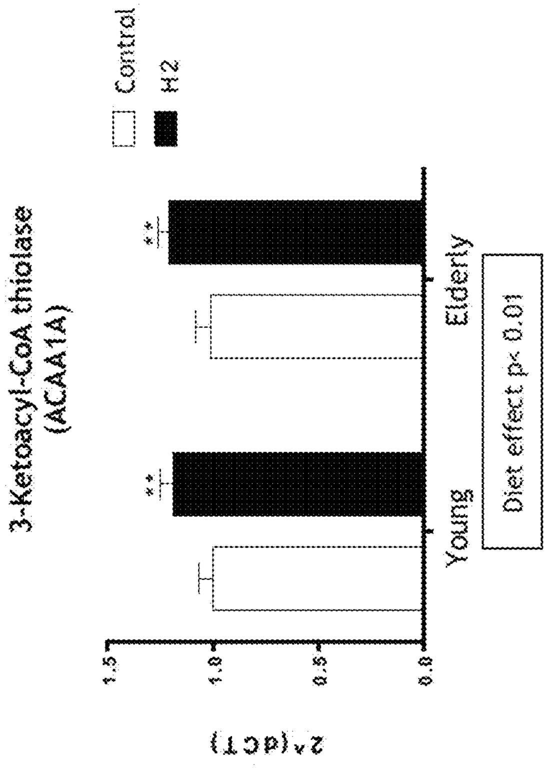
Fig. 11 (Continued)

LPS effect p<0.001
Supplementation effect p<0.001

LPS effect p<0.05
Supplementation effect p<0.05

| Oxylipin | Control | | H2 | |
|---|---|---|---|---|
| | Saline | LPS | Saline | LPS |
| **AA-oxylipins** | | | | |
| **Thromboxanes, prostaglandins** | | | | |
| TxB2 | 1584.36 ± 136.93 | 1739.60 ± 138.94 | 1729.72 ± 220.19 | 1495.16 ± 30.78 |
| 6kPGF1 α | 151.68 ± 68.79[a] | 505.96 ± 66.67[a b c] | 246.65 ± 83.26 | 78.59 ± 49.27[b] |
| PGF2 α | 4429.79 ± 380.97[a b c] | 5550.45 ± 330.52[a] | 4582.04 ± 486.14[b] | 5708.87 ± 577.25 |
| PGE2 | 1428.02 ± 141.17[a] | 2366.56 ± 121.53[a] | 1410.87 ± 117.93[b] | 2356.64 ± 224.38[b] |
| PGD2 | 1741.08 ± 319.14[a] | 3208.60 ± 445.99[a c] | 1639.05 ± 216.33[b] | 3188.42 ± 282.95[b] |
| PGA1 | 0.00 ± 0.00[a] | 28.65 ± 7.78[a c] | 0.00 ± 0.00[b] | 34.75 ± 11.80[b d] |
| 15dPGJ2 | 31.15 ± 19.37 | 71.23 ± 8.44 | 13.59 ± 13.59 | 89.69 ± 19.08 |
| 8isoPGA2 | 464.81 ± 24.87 | 651.95 ± 76.86 | 500.41 ± 109.57 | 864.62 ± 133.33 |
| **Lipoxins** | | | | |
| LxA4 | 265.31 ± 31.85[a b] | 764.10 ± 117.00[a c] | 352.61 ± 37.66[d] | 1126.31 ± 115.00[c d e] |
| LxB4 | 119.60 ± 79.81 | 413.04 ± 100.91 | 488.09 ± 79.65 | 560.64 ± 67.12 |
| **Epoxy-eicosatrienoic acids** | | | | |
| 14,15-EET | 258.15 ± 55.32 | 218.68 ± 27.43 | 221.62 ± 44.03 | 339.82 ± 95.94 |
| 8,9-EET | 665.74 ± 86.14 | 717.35 ± 62.99 | 745.55 ± 88.82 | 1132.12 ± 251.53 |
| 5,6-EET | 510.40 ± 59.39 | 552.36 ± 22.88 | 607.26 ± 61.65 | 776.15 ± 152.98 |
| **Hydroxy eicosatrienoic acids** | | | | |
| 15-HETE | 5381.63 ± 491.85[a b] | 10236.55 ± 1133.60[a] | 4986.08 ± 394.85[c d] | 12370.92 ± 946.68[c e] |
| 8-HETE | 616.39 ± 59.62[a] | 861.88 ± 71.18[a d] | 536.21 ± 32.63[b c] | 1094.93 ± 100.61[b d e] |
| 12-HETE | 1496.97 ± 53.35[a] | 2662.28 ± 394.98[a] | 1188.01 ± 51.49[b c] | 3479.62 ± 252.58[c d] |
| 5-HETE | 5518.82 ± 671.54 | 6747.00 ± 403.13 | 5484.87 ± 486.33 | 8002.11 ± 382.00 |
| 5-oxoETE | 5524.57 ± 639.67[a] | 6300.15 ± 474.39[d] | 5286.41 ± 199.95[b c] | 9143.13 ± 785.06[c d] |
| **LA-oxylipins** | | | | |
| 13-HODE | 1294.54 ± 41.33 | 2091.36 ± 184.04[b] | 1429.20 ± 192.49[a] | 3655.32 ± 871.76[a b c] |
| 9-HODE | 497.38 ± 19.99[a b] | 979.03 ± 109.81[a d] | 577.19 ± 76.69[c] | 1628.83 ± 355.30[c d e] |
| **DHA-oxylipins** | | | | |
| 17-HDoHE | 1208.83 ± 91.11[a] | 2030.94 ± 216.72[a] | 1002.70 ± 83.64[b c] | 2428.07 ± 154.48[b d] |
| 14-HDoHE | 819.92 ± 71.54[a] | 1171.61 ± 168.81[d] | 639.76 ± 45.18[b c] | 1683.52 ± 143.81[b d] |
| 7-MaR1 | 0.00 ± 0.00[a] | 42.73 ± 11.82[a c] | 0.00 ± 0.00[b] | 88.89 ± 50.81[b d] |
| | | | | |

Fig. 16

| Oxylipin | DHA | | Statistical effect | | |
|---|---|---|---|---|---|
| | Saline | LPS | Supplementation | LPS | Supplementation x LPS |
| **AA-oxylipins** | | | | | |
| Thromboxanes, prostaglandins | | | | | |
| TxB2 | 1781.36 ± 166.54 | 1747.47 ± 205.07 | - | - | - |
| 6kPGF1 α | 210.93 ± 69.00 | 226.75 ± 92.39[c] | - | - | p<0.01 |
| PGF2 α | 5656.33 ± 461.46[c] | 5155.75 ± 727.26 | p<0.01 | p<0.001 | p<0.001 |
| PGE2 | 1883.66 ± 204.02 | 1881.02 ± 257.90 | - | p<0.001 | p<0.05 |
| PGD2 | 2301.83 ± 244.21 | 2178.11 ± 411.06[c] | - | p<0.01 | p<0.05 |
| PGA1 | 0.00 ± 0.00 | 0.00 ± 0.00[c d] | p<0.01 | p<0.001 | p<0.01 |
| 15dPGJ2 | 45.69 ± 23.73 | 53.66 ± 24.59 | - | p<0.05 | - |
| 8isoPGA2 | 682.20 ± 116.56 | 750.64 ± 92.68 | - | p<0.05 | - |
| Lipoxins | | | | | |
| LxA4 | 631.05 ± 121.16[b] | 614.25 ± 151.20[c] | - | p<0.001 | p<0.01 |
| LxB4 | 342.60 ± 115.89 | 309.99 ± 112.83 | p<0.05 | - | - |
| Epoxy-eicosatrienoic acids | | | | | |
| 14,15-EET | 317.46 ± 68.49 | 321.12 ± 36.59 | - | - | - |
| 8,9-EET | 984.20 ± 127.64 | 904.92 ± 119.39 | - | - | - |
| 5,6-EET | 730.88 ± 94.28 | 687.14 ± 90.15 | - | - | - |
| Hydroxy eicosatrienoic acids | | | | | |
| 15-HETE | 8412.97 ± 1033.41[b d] | 8271.61 ± 1124.26[c] | - | p<0.001 | p<0.01 |
| 8-HETE | 825.45 ± 81.77[c] | 823.81 ± 84.78[c] | - | p<0.001 | p<0.01 |
| 12-HETE | 2076.89 ± 258.48[b] | 2145.92 ± 439.72[d] | - | p<0.001 | p<0.01 |
| 5-HETE | 7715.60 ± 1005.41 | 8939.82 ± 1212.00 | p<0.05 | p<0.05 | - |
| 5-oxoETE | 8623.43 ± 291.86[a b] | 7449.52 ± 981.74 | p<0.01 | p<0.05 | p<0.01 |
| **LA-oxylipines** | | | | | |
| 13-HODE | 2266.32 ± 315.64 | 2212.73 ± 339.80[c] | - | p<0.01 | p<0.05 |
| 9-HODE | 967.76 ± 132.13[b] | 950.78 ± 147.61[c] | - | p<0.001 | p<0.01 |
| DHA-oxylipins | | | | | |
| 17-HDoHE | 1717.12 ± 318.00[c] | 1731.76 ± 194.06[d] | - | p<0.001 | p<0.01 |
| 14-HDoHE | 1266.36 ± 187.27[a c] | 1290.20 ± 175.01 | - | p<0.001 | p<0.01 |
| 7-MaR1 | 0.00 ± 0.00 | 0.00 ± 0.00[c d] | p<0.01 | p<0.001 | p<0.01 |

Fig. 16 (Continued)

PROTEIN HYDROLYSATE DERIVED FROM BLUE-BACKED FISH

FIELD

This invention relates to functional protein hydrolysates. More precisely, it concerns a protein hydrolysate obtained from at least one blue fish protein source comprising (i) a degree of hydrolysis (DH) of at least 10%, (ii) at least 80% of water-soluble proteins with a molecular weight of less than 1000 Da, (iii) at least 0.3% of phospholipids, and (iv) at least 0.5% of DHA and EPA It further relates to food or pharmaceutical compositions comprising said protein hydrolysate and their use for the prevention and/or treatment of mild age-related cognitive disorders.

BACKGROUND

Ageing populations is one of the greatest economic and social challenges of the 21st century (1). By 2040, the number of people in the world over 65 is expected to more than double, from 506 million in 2008 to 1.3 billion, according to a 2009 US study (2). By 2025, more than 148 million people in Europe will be over 65 (>20% of the population) compared to 120 million in 2010, with a particularly rapid increase in the number of octogenarians. Ageing is accompanied in humans by the appearance of specific symptoms, in particular cognitive decline linked to cerebral ageing (3). It is a non-pathological but significant alteration of brain functions, including memory and vigilance disorders, which can lead to a loss of autonomy and can sometimes herald neurodegenerative diseases. Finding solutions to enable people to age in good health for as long as possible is therefore essential and constitutes a real economic, societal and public health challenge for developed countries. The concept of "healthy ageing" (4) or "successful ageing" integrates these different aspects and the era of 4P medicine (more preventive, predictive, personalised, participative) into which we are entering should, in the years to come, give pride of place to prevention, particularly through nutrition, and to each individual taking responsibility for his or her own health.

Similarly, the life expectancy of pets, especially cats and dogs, is increasing steadily due to improved nutrition and care. In the United States, for example, the average lifespan of dogs was 11 years in 2012 (+0.5 years compared to 2002), while for cats it was 12 years in the same year (+1 year compared to 2002) (5). In the United States, it is estimated that 30-40% of the total dog population is over 7 years old. In Europe, the less accurate estimate puts this proportion at 25-45%.

As with humans, the increasing life expectancy of pets raises real challenges in maintaining satisfactory living conditions for older individuals. One of the main challenges is to reduce the incidence of age-related neurodegenerative diseases, or at least to delay them. Among these diseases, the cognitive dysfunction syndrome (CDS) is well characterised in dogs. Its behavioural manifestations are loss of orientation, alterations in the relationship with the owner and changes in sleep-wake cycles (6). These effects are also seen in older cats (6). Epidemiological studies indicate that CDS affects 5% of dogs aged 10-12 years, 23% of dogs aged 12-14 years, and 41% of dogs aged over 14 years (7).

To meet these challenges, there is a need for new products capable of preventing age-related cognitive decline and associated disorders in both humans and animals, and thus of maintaining the quality of life and autonomy of older individuals for longer.

The beneficial effects of eating fatty and lean fish have been known for a long time, and today there is a real consumer interest in seafood. It is known that oily fish in general, and blue fish in particular, are rich in polyunsaturated fatty acids (PUFAs), notably EPA (eicosapentaenoic acid) and DHA (docosahexaenoic acid), phospholipids, and proteins.

However, to the best of the inventors' knowledge, there is no product or ingredient on the nutraceutical or pet food market that contains a significant amount of these active ingredients of interest for the brain, obtained by an ecologically friendly process using a unique marine resource, in particular blue fish such as sardines.

The inventors have thus developed a particularly innovative hydrolysis process, making it possible to obtain blue fish hydrolysates with beneficial effects for the prevention of age-related cognitive decline. Rich in bioactive peptides combined with DHA and phospholipids, such a hydrolysate has beneficial effects in neuroprotection, cognitive enhancement and stress/anxiety reduction.

SUMMARY

One aim of the invention is therefore to provide a "3-in-1" product containing at least 3 active ingredients of interest for the brain, in particular peptides, phospholipids and DHA, making it possible to prevent and/or treat age-related cognitive decline and associated disorders in humans and animals.

To this end, according to a first aspect of the invention, a protein hydrolysate obtained from at least one protein source from blue fish, in particular at least from blue fish heads, is proposed, comprising:

(i) a degree of hydrolysis (DH) of at least 10%,
(ii) at least 80% water-soluble protein with a molecular weight of less than 1000 Da,
(iii) at least 0.3% phospholipids, and
(iv) at least 0.5% DHA and EPA.

The invention also relates to a food composition comprising at least one protein hydrolysate according to the invention, characterised in that it is a complete food or a food supplement, in particular a functional food or nutraceutical, said food composition being intended for humans or animals.

Another object of this invention relates to a preparation process of a protein hydrolysate according to the invention comprising the steps of:

a. provision of a protein source;
b. grinding of said protein source;
c. optionally, pH adjustment;
d. addition of at least one hydrolysis enzyme;
e. heating;
f.
separation;
g. drying.

Lastly, the invention relates to a protein hydrolysate according to the invention or a pharmaceutical composition containing it, for use as a medicinal product.

BRIEF DESCRIPTION OF THE FIGURES

All figures illustrate embodiments of pure powdered hydrolysates according to the present invention.

FIG. 4: Effect of H2 hydrolysate supplementation on anxiety-like behaviour and corticosterone levels in young and old mice (n=11-13 per group; $p<0.05, $$p<0.01; diet effect **p<0.01).

FIG. 16: Effect of 18-day supplementation with H2 hydrolysate or DHA on oxylipin content in mouse hippocampus in response to LPS, (n=4-6 per group; values with superscripts (a, b, c, d, e) differ significantly).

DETAILED DESCRIPTION

Figure 1A:
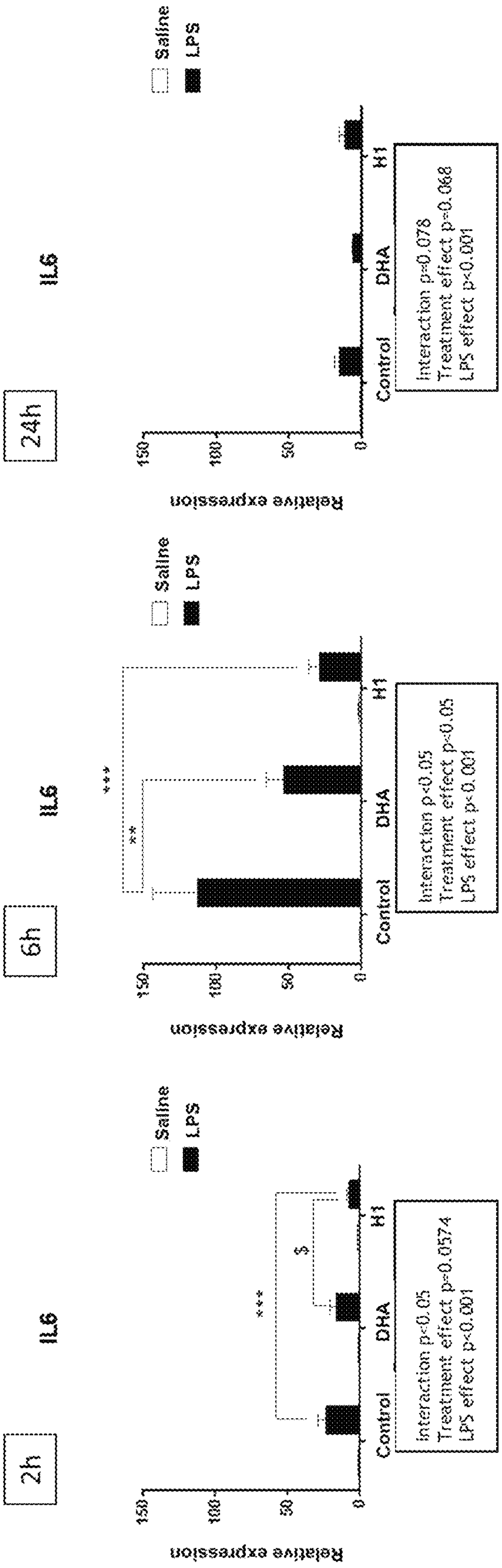
FIG. 1*a*: In vitro effect of H1 hydrolysate or DHA on the expression of the pro-inflammatory cytokine IL-6 in BV2 microglial cells after 2 h, 6 h and 24 h of LPS treatment (n=9; p<0.01, *p<0.001 LPS Control vs LPS Treatment, $p<0.05, $$p<0.01 DHA LPS vs H1 LPS).

Unless specifically stated otherwise, percentages are expressed here by weight of a reference product.

In this description, the intervals are defined in an abbreviated form to avoid reproducing them in full and to describe each and every value in the interval. Any appropriate value in the range can be chosen as the upper value, the lower value or the terminal values of the range. For example, an interval of 0.1 to 1.0 represents the terminal values of 0.1 and 1.0, as well as the intermediate values of 0.2, 0.3, 0.4, 0.5, 0.6, 0.7, 0.8, 0.9, and all intermediate intervals within 0.1 to 1.0, such as 0.2 to 0.5, 0.2 to 0.8, 0.7 to 1.0, etc. An interval defined as "between value A and value B" includes values A and B and is therefore equivalent to an interval "from value A to value B". In addition, the term "at least" includes the value set out below. For example, "at least 5%" should be understood as including "5%". The term "a maximum of" includes the value set out below. For example, "a maximum of 5%" should be understood as including "5%".

Furthermore, in this invention, measurable values, such as a quantity, are to be understood as including standard deviations which can easily be determined by the person skilled in the art pertaining to the technical field of reference. Preferably, these values are intended to include variations of ±5%.

As used throughout this document, the singular form of a word includes the plural and vice versa, unless the context clearly indicates otherwise. Thus, references to "a", "one" and "the" usually include the plurals of the respective terms. For example, a reference to a "process" or "food" includes a plurality of such "processes" or "foods". Similarly, the words "understand", "understands" and "understanding" will be interpreted inclusively. Similarly, the terms "include", "including" and "or" should all be considered inclusive. All of these terms should, however, be taken to encompass exclusive modes of implementation which may also be referred to using terms such as "consists of".

The processes and compositions and other embodiments illustrated herein are not limited to particular methodologies, protocols and reagents described herein as they may vary as will be understood by the person skilled in the art.

Unless otherwise indicated, all technical and scientific terms, terms used in the art and acronyms used herein have the meanings commonly accepted by the person skilled in the art in the field(s) of the invention, or in the field(s) in which the term is used. Although any composition, process, article of manufacture or other means or materials similar or equivalent to those described herein may be used in the practice of the present invention, the preferred compositions, processes, manufactured articles or other means or materials are described herein.

The inventors have developed a blue fish hydrolysate. The compounds of interest in bluefish, and in particular proteins, DHA and phospholipids, are combined in the hydrolysate according to the invention. Particularly advantageously, the inventors have optimised the proportions of these compounds of interest to enable beneficial biological effects to be achieved. In particular, the hydrolysate comprises a large proportion of protein, mainly in the form of peptides. This hydrolysate, rich in bioactive peptides and including phospholipids and DHA, has beneficial effects in the prevention of cognitive decline and anxiety, particularly related to age.

Protein Hydrolysate

In the context of this invention, several calculation methods have been used, in particular to determine the molecular weight profiles of proteins and/or peptides, the quantities of proteins, in particular soluble proteins, the quantities of phospholipids, DHA, EPA and other components of said hydrolysate. The calculation methods and/or reference articles detailing these methods are all presented in Example 1.7.

The content values mentioned in this text refer to the dried hydrolysate powder without the aid of a drying medium (referred to as "pure hydrolysate powder"). However, in the process of obtaining the hydrolysate, a drying support can advantageously be used to facilitate the implementation of the drying step on a large scale. In this case, a "powdered hydrolysate with medium" will be obtained, including a proportion of drying medium. Typically, 2-20%/w drying medium of the liquid hydrolysate before drying is used. Thus, to find out the content values of the hydrolysate powder with medium, it will be sufficient to adapt the content values provided in this text with reference to the pure hydrolysate powder in proportion to the amount of pure hydrolysate powder contained in the hydrolysate powder with medium.

According to a first aspect, the invention relates to a protein hydrolysate obtained from at least one blue fish protein source comprising:

(i) a degree of hydrolysis (DH) of at least 10%, (ii) at least 80% water-soluble protein with a molecular weight of less than 1000 Da, (iii) at least 0.3% phospholipids, and (iv) at least 0.5% DHA and EPA.

Blue fish are deep-sea pelagic fish. The blue fish gets its name from the colour of its skin, which is influenced by the accumulation of fat, especially omega-3 fatty acids, in its muscles. The blue fish covered by this invention are small blue fish chosen from the Family Clupeidae, and in particular sardines (*Sardina pilchardus, Sardinops* sp, *Sardinella* sp.) or herring (*Clupea harengus*); anchovies (*Engraulis encrasicolus*), mackerel (*Scomber scombrus*) and fish of the genus *Trachurus*.

The protein hydrolysate of this invention is thus obtained by hydrolysis of a protein source from blue fish. Degree of hydrolysis" (DH) means the percentage of peptide bonds broken during protein hydrolysis.

The hydrolysate of the invention has a degree of hydrolysis of at least 10%, said DH being determined by the pH-stat method as described by J. Adler-Nissen (17). Preferably, the degree of hydrolysis is greater than 11%. In particular, the degree of hydrolysis of said protein source is less than 20%, preferably less than 18%, preferably less than 17%, more preferably less than 16%, most preferably less than 15%. Obtaining such a degree of hydrolysis advantageously allows to have the bioactive peptides and lipids of interest in the hydrolysate according to the invention.

The hydrolysate according to the invention comprises in particular at least 45%, preferably at least 50%, more preferably at least 55%, even more preferably at least 60%, most preferably at least 65% of total protein (% by weight of pure hydrolysate powder). Said hydrolysate comprises in particular a maximum of 95%, preferably a maximum of 90%, more preferably a maximum of 85%, even more preferably a maximum of 80% of total protein (% by weight of pure hydrolysate powder).

According to a particular embodiment, the hydrolysate according to the invention comprises at least 45%, preferably at least 50%, more preferably at least 55%, even more preferably at least 60%, most preferably at least 65% soluble protein (% by weight of pure hydrolysate powder). Said hydrolysate comprises in particular a maximum of 95%, preferably a maximum of 90%, more preferably a maximum of 85%, even more preferably a maximum of 80%, most preferably a maximum of 75% of soluble proteins (% by weight of pure hydrolysate powder).

A wide spectrum of biological activities is attributed to the peptides composing the hydrolysates: anti-hypertensive, hypocholesterolemic, immuno-modulating, anti-microbial, anti-oxidant and opioid (or anti-stress) activities, etc. Generally speaking, bioactive peptides generally contain 4 to 20 amino acids. This makes them more resistant to the action of digestive enzymes, while their small size allows them to cross the intestinal barrier and enter the bloodstream. Advantageously, the protein hydrolysate of the invention is rich in peptides. In particular, it comprises at least 80% of water-soluble proteins with a molecular weight of less than 1000 daltons (Da) (peptides). In the context of this invention, the expression "proteins of molecular weight XX Da" refers to amino acids and/or peptides and/or proteins, depending on the molecular weight value. "Peptides" are defined in particular by a molecular weight of less than 1000 Da. In particular, the protein hydrolysate of the invention comprises at least 80% water-soluble proteins of molecular weight less than 1000 Da, preferably at least 83% water-soluble proteins of molecular weight less than 1000 Da, more preferably at least 84% water-soluble proteins of molecular weight less than 1000 Da, more preferably at least 85% water-soluble proteins of molecular weight less than 1000 Da, most preferably at least 86% water-soluble proteins of molecular weight less than 1000 Da. Said hydrolysate contains a maximum of According to a particular embodiment, the hydrolysate according to the invention has the following molecular weight profile:

at least 50%, preferably at least 55%, more preferably at least 60%, more preferably at least 65%, more preferably at least 68% of water-soluble proteins with a molecular weight of less than 500 Da, and preferably a maximum of 95%, more preferably a maximum of 90%, more preferably a maximum of 85%, more preferably a maximum of 82%, more preferably a maximum of 80% of water-soluble proteins with a molecular weight of less than 500 Da;

at least 8%, preferably at least 8.5%, more preferably at least 9%, more preferably at least 9.5%, preferably at least 10%, of water-soluble proteins with a molecular weight between 500 Da and 1000 Da, and preferably a maximum of 35%, preferably a maximum of 30%, preferably a maximum of 25%, preferably a maximum of 22%, preferably a maximum of 20%, preferably a maximum of 18%, preferably a maximum of 17% of water-soluble proteins with a molecular weight between 500 Da and 1000 Da;

at least 7%, preferably at least 7.5%, more preferably at least 8%, more preferably at least 8.5%, more preferably at least 9% of water-soluble proteins with a molecular weight between 1000 Da and 5000 Da, and preferably a maximum of 20%, more preferably a maximum of 18%, more preferably a maximum of 16%, more preferably a maximum of 15%, more preferably a maximum of 14% of water-soluble proteins with a molecular weight between 1000 Da and 5000 Da;

at least 0.10%, preferably at least 0.15%, more preferably at least 0.20%, more preferably at least 0.25%, more preferably at least 0.30% of water-soluble proteins with a molecular weight of more than 5000 Da, and preferably a maximum of 2.0%, more preferably a maximum of 1.5%, more preferably a maximum of 1.0%, more preferably a maximum of 0.8%, more preferably a maximum of 0.7% of water-soluble proteins with a molecular weight of more than 5000 Da.

The hydrolysate preferably comprises between 12% and 35%, more preferably between 15% and 32%, even more preferably between 17% and 30%, even more preferably between 20% and 28%, most preferably between 22% and 26% of free amino acids in relation to the total proteins.

In particular, the hydrolysate preferably comprises between 0.3% and 2.0%, more preferably between 0.4 and 1.8%, even more preferably between 0.5% and 1.5%, even more preferably between 0.6% and 1.3%, most preferably between 0.7% and 1.0% tryptophan (% by weight of pure hydrolysate powder).

In particular, the hydrolysate preferably comprises between 3.0% and 9.0%, more preferably between 3.5% and 8.5%, more preferably between 4.0% and 8.0%, most preferably between 4.5% and 7.5%, most preferably between 5.0% and 7.0% lysine (% by weight of pure hydrolysate powder).

In particular, the hydrolysate comprises between 3% and 20%, preferably further between 5% and 18%, more preferably between 7% and 16%, even more preferably between 9% and 15%, most preferably between 10% and 14% of branched-chain amino acids (% by weight of pure hydrolysate powder). Branch chain amino acids are defined as isoleucine, leucine and valine.

In particular, the hydrolysate comprises between 0.5% and 8%, preferably further between 1% and 7%, more preferably between 1.5% and 6%, most preferably between 1.8% and 5%, most preferably between 2% and 4% of sulphur-containing amino acids (% by weight of pure hydrolysate powder). Sulphur-containing amino acids are cystine, cysteine and methionine.

In particular, the hydrolysate comprises between 15% and 45%, preferably further between 17% and 42%, more preferably between 20% and 39%, most preferably between 23% and 36%, most preferably between 25% and 34% of essential amino acids (% by weight of pure hydrolysate powder). In particular, the hydrolysate comprises between 5% and 20%, preferably further between 6% and 18%, more preferably between 7% and 16%, most preferably between 8% and 14%, most preferably between 9% and 12% of free essential amino acids (% by weight of pure hydrolysate powder). Essential amino acids are lysine, methionine, cystine, threonine, tryptophan, phenylalanine, tyrosine, valine, leucine, isoleucine (for humans).

The hydrolysate according to the invention has in particular a total fat content of at least 3%, preferably at least 4%, more preferably at least 5%, even more preferably at least 6%, most preferably at least 7% (% by weight of pure hydrolysate powder). Said hydrolysate comprises in particular a total fat content of less than or equal to 20%, preferably less than or equal to 19%, even more preferably less than or equal to 18%, most preferably less than or equal to 17%, most preferably less than or equal to 16% (% by weight of pure hydrolysate powder).

"Total fat" means the total of neutral lipids and polar lipids (or phospholipids), which corresponds to "total lipids".

Among the lipids present, the protein hydrolysate of the invention advantageously contains phospholipids (or polar lipids). Phospholipids are structural lipids, the main constituents of membranes. The fatty acids associated (C20 and C22) with phospholipids have an essential role in the plasma membrane since they ensure the improvement of its fluidity thanks to two elements, the length of the chains and the rotations allowed by the double bonds.

The protein hydrolysate of the invention comprises at least 0.3% phospholipids (% by weight of pure hydrolysate powder). In particular, it comprises at least 0.35% phospholipids, preferably at least 0.4% phospholipids, even more preferably at least 0.45% phospholipids, even more preferably at least 0.5% phospholipids, even more preferably at least 0.55% phospholipids, most preferably at least 0.60% phospholipids (wt. % of pure hydrolysate powder). In embodiments of the invention, the protein hydrolysate comprises at least 1% phospholipids (% by weight of pure hydrolysate powder). In particular, it comprises at least 1.1% phospholipids, preferably at least 1.2% phospholipids, more preferably at least 1.3% phospholipids, even more preferably at least 1.4% phospholipids, most preferably at least 1.5% phospholipids (% by weight of pure hydrolysate powder). Said hydrolysate contains a maximum of 3% phospholipids, preferably a maximum of 2.8% phospholipids, more preferably a maximum of 2.5% phospholipids, most preferably a maximum of 2.3% phospholipids, most preferably a maximum of 2.1% phospholipids (% by weight of pure hydrolysate powder).

In particular, the phospholipids represent at least 4%, preferably at least 4.5%, more preferably at least 5%, even more preferably at least 5.5%, even more preferably at least 6%, most preferably at least 6.5% of the total fat of the pure hydrolysate powder according to the invention. In particular embodiments, the phospholipids represent at least 10%, preferably at least 11%, more preferably at least 12%, even more preferably at least 14%, most preferably at least 15% of the total fat of the pure powdered hydrolysate according to the invention. In particular, the phospholipids represent a maximum of 70%, preferably a maximum of 65%, even more preferably a maximum of 60%, even more preferably a maximum of 55%, most preferably a maximum of 50% of the total fat of the pure hydrolysate powder according to the invention.

According to a preferred embodiment, the hydrolysate of the invention is rich in phosphatidylserine (PS), phosphatidylethanolamine (PE), phosphatidylcholine (PC) and phosphatidylinositol (PI), four phospholipids predominant in the brain.

According to this embodiment, said hydrolysate contains in particular phosphatidylserine in an amount of at least 0.1 mg, preferably at least 0.2 mg, more preferably at least 0.3 mg, even more preferably at least 0.4 mg, most preferably at least 0.5 mg, per gram of pure hydrolysate in powder form.

According to this embodiment, said hydrolysate contains in particular phosphatidylserine in an amount less than or equal to 5 mg, preferably less than or equal to 4 mg, even more preferably less than or equal to 3 mg, even more preferably less than or equal to 2.5 mg, most preferably less than or equal to 2 mg, per gram of pure hydrolysate powder.

Said hydrolysate also contains phosphatidylethanolamine in an amount of at least 0.1 mg, preferably at least 0.2 mg, more preferably at least 0.25 mg, most preferably at least 0.3 mg, most preferably at least 0.35 mg, per gram of pure hydrolysate powder. In particular embodiments, said hydrolysate contains phosphatidylethanolamine in an amount of at least 0.5 mg, preferably at least 0.8 mg, more preferably at least 1.2 mg, most preferably at least 1.4 mg, most preferably at least 1.5 mg, per gram of pure hydrolysate powder.

Said hydrolysate also contains phosphatidylethanolamine in an amount less than or equal to 7 mg, preferably less than or equal to 6 mg, more preferably less than or equal to 5 mg, most preferably less than or equal to 4.5 mg, most preferably less than or equal to 4 mg, per gram of pure hydrolysate powder.

Said hydrolysate further contains phosphatidylcholine in an amount of at least 1 mg, preferably at least 1.5 mg, more preferably at least 2 mg, even more preferably at least 2.5 mg, even more preferably at least 3 mg, most preferably at least 3.5 mg, per gram of pure hydrolysate powder. In particular embodiments, said hydrolysate contains phosphatidylcholine in an amount of at least 5 mg, preferably at least 6 mg, more preferably at least 6.5 mg, even more preferably at least 7 mg, most preferably at least 7.5 mg, per gram of pure hydrolysate powder.

Said hydrolysate further contains phosphatidylcholine in an amount less than or equal to 20 mg, preferably less than or equal to 18 mg, more preferably less than or equal to 16 mg, most preferably less than or equal to 14 mg, most preferably less than or equal to 12.5 mg, per gram of pure hydrolysate powder.

Said hydrolysate also contains phosphatidylinositol in an amount of at least 0.2 mg, preferably at least 0.3 mg, more preferably at least 0.4 mg, most preferably at least 0.45 mg, most preferably at least 0.5 mg, per gram of pure hydrolysate powder. In particular embodiments, said hydrolysate contains phosphatidylinositol in an amount of at least 0.5 mg, preferably at least 0.7 mg, more preferably at least 0.9 mg, even more preferably at least 1 mg, most preferably at least 1.1 mg, per gram of pure hydrolysate powder.

Said hydrolysate also contains phosphatidylinositol in an amount less than or equal to 5 mg, preferably less than or equal to 4 mg, more preferably less than or equal to 3 mg, most preferably less than or equal to 2.5 mg, most preferably less than or equal to 2.1 mg, per gram of pure hydrolysate powder.

Polyunsaturated fatty acids (PUFAs) are fatty acids with at least two double bonds in their hydrocarbon chain. Among the different families of PUFAs, two families, the n-6 (or omega 6) and n-3 (or omega 3) PUFAs are of great nutritional interest. They differ in the position of the first double bond. These two families are derived from metabolic precursors of exclusively plant origin: alpha linolenic acid (n-3) (ALA) and linoleic acid (n-6) (LA), which must therefore be provided by our diet. These are essential fatty acids. ALA is mainly found in rapeseed, soy bean, walnut and flaxseed seeds and oils and LA in sunflower, peanut, corn and grape seed seeds and oils. Once consumed, ALA is converted into derivatives essential for health: eicosapentaenoic acid (EPA) and docosahexaenoic acid (DHA). Marine fish, which feed on algae and phytoplankton, are a good source of EPA and DHA. LA is metabolised into arachidonic acid (AA), which is also essential for health, and is directly supplied by the consumption of products from land animals (eggs, meat).

The PUFAs present in the brain are mainly AA and DHA, which are constituents of the brain membranes. The incorporation of PUFAs is highest during brain development, while in the adult brain, DHA and AA no longer accumulate, but their levels are maintained by a regular turnover that compensates for their use. These levels likely vary according to dietary intake.

Advantageously, the hydrolysate according to the invention contains polyunsaturated fatty acids (PUFAs), and in particular a significant proportion of omega 3. In particular, it comprises at least 0.5%, preferably at least 1%, more preferably at least 1.5%, even more preferably at least 2%, most preferably at least 2.5% of polyunsaturated fatty acids (PUFA), and in particular omega 3 and omega 6 (% by weight of pure hydrolysate powder). Preferably, said hydrolysate contains a maximum of 5%, preferably a maximum of 4.7%, more preferably a maximum of 4.5%, even more preferably a maximum of 4.2%, most preferably a maximum of 4.0% of polyunsaturated fatty acids (PUFA), and in particular omega 3 and omega 6 (% by weight of pure hydrolysate powder).

Preferably, the hydrolysate according to the invention comprises at least 0.5%, preferably at least 0.7%, more preferably at least 1%, most preferably at least 1.5%, most preferably at least 2% omega 3 (% by weight of pure hydrolysate powder). Preferably, said hydrolysate contains a maximum of 4%, preferably a maximum of 3.9%, more preferably a maximum of 3.8%, more preferably a maximum of 3.7%, most preferably a maximum of 3.5% omega 3 (% by weight of pure hydrolysate powder).

In particular, the omega-3 represents at least 15%, preferably at least 20%, more preferably at least 25%, even more preferably at least 30% of the total fat of the pure hydrolysate powder according to the invention. In particular, the omega-3 represents at most 50%, preferably at most 45%, even more preferably at most 40%, even more preferably at most 35% of the total fat of the pure hydrolysate powder according to the invention.

In particular, the hydrolysate according to the invention comprises at least 0.05%, preferably at least 0.07%, more preferably at least 0.1%, most preferably at least 0.15%, most preferably at least 0.2% of omega 6 (% by weight of pure hydrolysate powder). Preferably, said hydrolysate contains a maximum of 1.5%, preferably a maximum of 1.4%, more preferably a maximum of 1.3%, more preferably a maximum of 1.2%, most preferably a maximum of 1.1% omega 6 (% by weight of pure hydrolysate powder).

In particular, omega 6 represents at least 0.5%, preferably at least 0.75%, more preferably at least 1%, even more preferably at least 2% of the total fat of the pure hydrolysate powder according to the invention. In particular, omega 6 represents a maximum of 25%, preferably a maximum of 21%, even more preferably a maximum of 17%, even more preferably a maximum of 13% of the total fat of the pure hydrolysate powder according to the invention.

The hydrolysate of the invention is particularly advantageous due to the presence of DHA and EPA. The protein hydrolysate of the invention comprises at least 0.5% DHA and EPA (in % of pure hydrolysate powder). In particular it comprises at least 0.7% DHA and EPA, preferably at least 0.9% DHA and EPA, even more preferably at least 1% DHA and EPA, most preferably at least 1.5% DHA and EPA (% by weight of pure hydrolysate powder).

Preferably, said hydrolysate contains a maximum of 5% DHA and EPA, preferably a maximum of 4.5% DHA and EPA, more preferably a maximum of 4% DHA and EPA, more preferably a maximum of 3.5% DHA and EPA, most preferably a maximum of 3.2% DHA and EPA (% by weight of pure hydrolysate powder).

In particular, DHA and EPA represent at least 10%, preferably at least 15%, more preferably at least 20%, even more preferably at least 22% of the total fat of the pure hydrolysate powder according to the invention. In particular, DHA and EPA represent a maximum of 40%, preferably a maximum of 35%, even more preferably a maximum of 30%, even more preferably a maximum of 27% of the total fat of the pure hydrolysate powder according to the invention.

According to another preferred embodiment, it contains in particular DHA in an amount of at least 2 mg, preferably at least 3 mg, more preferably at least 5 mg, even more preferably at least 7 mg, most preferably at least 9 mg, per gram of pure hydrolysate powder.

Said hydrolysate preferably contains DHA in an amount less than or equal to 30 mg, preferably less than or equal to 27 mg, more preferably less than or equal to 25 mg, most preferably less than or equal to 23 mg, most preferably less than or equal to 20 mg, per gram of pure hydrolysate powder.

In particular, DHA represents at least 5%, preferably at least 5.3%, more preferably at least 5.7%, even more preferably at least 5.9%, most preferably at least 6% of the total fat of the pure hydrolysate powder according to the invention. In particular, DHA represents at most 30%, preferably at most 27%, more preferably at most 25%, even more preferably at most 22%, most preferably at most 20% of the total fat of the pure hydrolysate powder according to the invention.

In combination with peptides, DHA, which is present but not predominant, has beneficial effects.

According to another preferred embodiment, said protein hydrolysate also contains EPA in an amount of at least 0.5 mg, preferably at least 1 mg, more preferably at least 2 mg, even more preferably at least 3 mg, most preferably at least 4 mg, per gram of pure hydrolysate powder.

Said hydrolysate preferably contains EPA in an amount less than or equal to 25 mg, preferably less than or equal to 24 mg, more preferably less than or equal to 23 mg, even more preferably less than or equal to 22 mg, most preferably less than or equal to 21 mg, most preferably less than or equal to 20 mg, per gram of pure hydrolysate powder.

In particular, EPA represents at least 1%, preferably at least 2%, more preferably at least 4%, even more preferably at least 6% of the total fat of the pure hydrolysate powder according to the invention. In particular, EPA represents at most 40%, preferably at most 35%, more preferably at most 30%, even more preferably at most 25% of the total fat of the pure hydrolysate powder according to the invention.

Particularly advantageously, a proportion of omega 3 in the hydrolysate according to the invention, and in particular DHA and EPA, is bound to phospholipids.

In particular, the hydrolysate according to the invention comprises at least 0.3%, preferably at least 0.35%, even more preferably at least 0.4%, most preferably at least 0.45%, most preferably at least 0.5% of omega 3 bound to phospholipids. Preferably, said hydrolysate contains a maximum of 1%, preferably a maximum of 0.95%, more preferably a maximum of 0.9%, most preferably a maximum of 0.85%, most preferably a maximum of 0.8% of phospholipid-bound omega-3.

More particularly, the hydrolysate according to the invention comprises at least 0.15%, preferably at least 0.20%, more preferably at least 0.25%, most preferably at least 0.30%, most preferably at least 0.35% of phospholipid-bound DHA. Preferably, said hydrolysate contains a maximum of 1%, preferably a maximum of 0.9%, more preferably a maximum of 0.8%, most preferably a maximum of 0.7%, most preferably a maximum of 0.65% DHA bound to phospholipids.

More particularly, the hydrolysate according to the invention comprises at least 0.050%, preferably at least 0.055%, more preferably at least 0.060%, most preferably at least 0.070%, most preferably at least 0.080% of EPA bound to phospholipids. Preferably, said hydrolysate contains a maximum of 0.2%, preferably a maximum of 0.18%, more preferably a maximum of 0.15%, most preferably a maximum of 0.13%, most preferably a maximum of 0.11% EPA bound to phospholipids.

In particular, the hydrolysate according to the invention comprises at least 0.005%, preferably at least 0.01%, even more preferably at least 0.015%, most preferably at least 0.02%, most preferably at least 0.025% of omega 6 bound to phospholipids. Preferably, said hydrolysate contains a maximum of 0.5%, preferably a maximum of 0.4%, more preferably a maximum of 0.3%, most preferably a maximum of 0.2%, most preferably a maximum of 0.15% of phospholipid-bound omega-6.

Neutral lipids" or "neutral fats" or "simple lipids", consisting mainly of triglycerides (or triacylglycerols), are the main form of fat storage in fat cells. According to a particular embodiment, the hydrolysate according to the invention comprises at least 0.1%, preferably at least 0.2%, more preferably at least 0.3%, most preferably at least 0.4%, most preferably at least 0.5% of neutral lipids, preferably triglycerides (% by weight of pure hydrolysate powder). Preferably, said hydrolysate contains a maximum of 15%, preferably a maximum of 14%, more preferably a maximum of 12%, even more preferably a maximum of 10% of neutral lipids, preferably triglycerides (% by weight of pure hydrolysate powder).

According to a particular embodiment, the hydrolysate according to the invention comprises at least 0.05 mg, preferably at least 0.10 mg, more preferably at least 0.15 mg, even more preferably at least 0.20 mg of plasmalogens per gram of pure hydrolysate powder. Preferably, said hydrolysate contains a maximum of 1.0 mg, preferably a maximum of 0.8 mg, more preferably a maximum of 0.7 mg, even more preferably a maximum of 0.5 mg of plasmalogens per gram of pure hydrolysate powder.

The hydrolysate can be in any form, including liquid or powder. According to a particular embodiment, the hydrolysate according to the invention is in powder form. According to this particular embodiment, the hydrolysate preferably comprises at least 1%, preferably at least 2% moisture, more preferably at least 3%, even more preferably at least 4% moisture (% by weight of pure hydrolysate powder). Furthermore, said hydrolysate comprises at most 15%, preferably at most 12%, more preferably at most 10%, even more preferably at most 9%, most preferably at most 8% moisture (% by weight of pure hydrolysate powder).

The hydrolysate contains minerals. In particular, the hydrolysate may preferably comprise at least 5%, preferably at least 6%, more preferably at least 7%, even more preferably at least 8%, most preferably at least 8.5% minerals (% by weight of pure hydrolysate powder). Furthermore, said hydrolysate comprises at most 20%, preferably at most 15%, more preferably at most 12%, even more preferably at most 11%, most preferably at most 10% minerals (% by weight of pure hydrolysate powder).

In particular, the hydrolysate preferably comprises between 2 mg and 8 mg, more preferably between 2.3 mg and 7.8 mg, even more preferably between 2.5 mg and 7.5 mg, even more preferably between 2.8 mg and 7.3 mg, most preferably between 3 mg and 7 mg of selenium per kilogram of pure hydrolysate powder according to the invention.

In particular, the hydrolysate preferably comprises between 12 mg and 60 mg, more preferably between 15 mg and 55 mg, more preferably between 18 mg and 50 mg, more preferably between 20 mg and 48 mg, most preferably between 22 mg and 45 mg of zinc per kilogram of pure powdered hydrolysate according to the invention.

In particular, the hydrolysate preferably comprises between 400 mg and 1500 mg, more preferably between 450 mg and 1450 mg, more preferably between 500 mg and 1400 mg, more preferably between 550 mg and 1350 mg, most preferably between 600 mg and 1300 mg of calcium per kilogram of pure hydrolysate powder according to the invention.

In particular, the hydrolysate preferably comprises between 2000 mg and 8000 mg, more preferably between 2150 mg and 7500 mg, even more preferably between 2300 mg and 7000 mg, even more preferably between 2500 mg and 6500 mg, most preferably between 2750 mg and 6000 mg of phosphorus per kilogram of pure hydrolysate powder according to the invention.

The hydrolysate preferably comprises between 0.01 mg and 1 mg, more preferably between 0.03 mg and 0.7 mg, more preferably between 0.05 mg and 0.5 mg, more preferably between 0.07 mg and 0.4 mg, most preferably between 0.1 mg and 0.2 mg of vitamin B12 per 100 grams of pure powdered hydrolysate according to the invention.

The hydrolysate preferably comprises between 0.004 mg and 0.06 mg, more preferably between 0.005 mg and 0.05 mg, more preferably between 0.006 mg and 0.04 mg, more preferably between 0.007 mg and 0.03 mg, most preferably between 0.008 mg and 0.02 mg of vitamin D3 per 100 grams of pure hydrolysate powder according to the invention.

In a preferred embodiment, the protein source used for the invention is at least from bluefish heads. In another preferred embodiment, said protein source is derived from sardines. In a preferred embodiment, said protein source is at least derived from sardine heads.

Sardines are small pelagic fish that feed on plankton, eggs and larvae of crustaceans. Its geographical range extends in particular from the central part of the North Sea to Cape Blanc in Mauritania. The species is also abundant in the Mediterranean as far as the Black Sea. Fatty fish having a lipid content varying from 3.2 to 15%, it is interesting for their nutritional qualities. Indeed, sardines are one of the richest fish in lipids and specifically in fatty acids of the omega 3 family (20 to 30% of total fatty acids) with a ratio of unsaturated fatty acids to saturated fatty acids close to 2. Sardines are low in carbohydrates (<0.1% by fresh weight) but are rich in proteins of very high nutritional value, a source of essential amino acids. 100 g of sardines are enough to cover 100% of daily amino acid requirements. In addition to the presence of quality proteins, long-chain PUFAs (polyunsaturated fatty acids) (EPA-DHA), phospholipids, etc., sardines also contain minerals such as iron and zinc; they contain little sodium but are rich in calcium, magnesium, potassium and selenium. It contains vitamins A, D, B3 (nicotinamide), B6 (pyridoxine), B12 (cobalamin) and E (d-tocopherol). A 150 g portion of sardines covers the daily requirement of vitamins D and E for a "standard" human being. It is also very interesting for its contribution in co-enzyme Q10. Sardines are fish at the beginning of the food chain, which has the advantage of containing low levels of heavy metal contaminants, such as methyl mercury, or PCBs.

According to another embodiment, the protein source used for the invention comprises bluefish heads, preferably said protein source is derived from heads alone. In an alternative embodiment, the protein source used for the invention comprises heads and viscera of blue fish, preferably said protein source is derived from heads and further comprises viscera, more preferably said protein source used for the invention is derived from heads and viscera. In a particular embodiment, the viscera represent less than 30% by weight of the protein source, preferably less than 20% by weight, more preferably less than 15% by weight. If the protein source comprises viscera, the endogenous enzymes of said viscera are preferably inactivated. This prevents autolysis of the protein source and produces a protein hydrolysate with standardised chemicophysical characteristics. Advantageously, the hydrolysate of the invention comprising heads and/or viscera makes it possible to add value to marine co-products, and to ensure sustainable fishing in the long term. These co-products, recovered during the processing of seafood (including filleting, gutting, heading etc.), are not normally consumed by humans. Obtaining these hydrolysates is thus a major strategic approach to rehabilitating the protein fraction of marine co-products.

Blue fish, and especially sardines, are therefore an excellent source of polyunsaturated fatty acids (PUFAs), omega-3 and omega-6, and in particular an excellent source of DHA. However, the amount and nature of the fatty acids may vary depending on the diet of the fish. The DHA content in hydrolysates may therefore be subject to certain variations depending on criteria such as the season or the fishing location. Thus, in a particular embodiment, the protein hydrolysate of the invention is supplemented with DHA. In other words, exogenous DHA or another source than the hydrolysate, comprising DHA, can be added to said hydrolysate according to the invention. In particular, the hydrolysate may be supplemented with DHA in a ratio of hydrolysate:DHA between 1:5 and 5:1, preferably between 1:2 and 2:1.

Process for Hydrolysis

Among the biotechnological processes offering a very dynamic field of research and industrial applications, the enzymatic hydrolysis of proteins makes it possible to generate a soluble fraction called "hydrolysate". Composed mainly of peptides and free amino acids, the hydrolysate of the invention is characterised by new functional, nutritional and biological properties, and has applications in human and animal nutrition and in the field of nutraceuticals and medicines. It is known to the person skilled in the art that the selection of the raw materials and the conditions of the hydrolysis reaction are decisive for obtaining a hydrolysate with a particular peptide and molecular profile. Furthermore, the biochemical properties of the hydrolysate determine its biological activity. Thus, two hydrolysates derived from the same protein source but with different peptide profiles or lipid content may not have the same level of activity, or even different biological activities.

"Protein source" or "protein material" or "protein fraction" or "protein substrate" means a material of natural origin, preferably of marine origin, preferably from blue fish, consisting in part of proteins and/or peptides and/or amino acids.

The enzymatic hydrolysis process developed in the context of the present invention is a gentle, solvent-free process that takes place in an aqueous medium: the blue fish co-products, in particular at least the blue fish heads, and preferably at least the sardine heads, are placed in the presence of a single enzyme or a mixture of enzymes, of the endo- and/or exopeptidase type, in a medium containing water, the pH and temperature of which have been adjusted in order to correspond to the optimum activity of the enzymes used (according to the manufacturers' recommendations). Enzymes break down the proteins contained in the co-products by breaking the peptide bonds between the amino acids that make up the proteins. As each enzyme has a selective action, the choice of enzyme(s) allows the specific targeting of the peptide bonds to be broken. The hydrolysates then undergo separation and drying steps to obtain a powder in a stabilised form.

"Endopeptidase enzyme" or "endoprotease" means a proteolytic enzyme capable of breaking peptide bonds within a peptide and/or protein, i.e. peptide bonds between non-terminal amino acids. Examples of endoproteases include:

- serine endopeptidases including trypsin, which cuts after the amino acids arginine or lysine, unless the latter is followed by proline; chymotrypsin, which cuts after the amino acids phenylalanine, tryptophan or tyrosine, unless followed by proline; elastase, which cuts after alanine, glycine, serine or valine residues, unless followed by proline; subtilisin, which catalyses protein hydrolysis with low peptide bond specificity and acts preferentially in the vicinity of a large uncharged amino acid residue;
- cysteine endopeptidases such as papain and ficin, which require the presence of a free —SH group in their active site to exert proteolytic action;
- aspartic acid endopeptidases such as pepsin, which contain an aspartic acid residue involved in catalysis in the active site. Pepsin cuts the bond before leucine, phenylalanine, tryptophan or tyrosine residues, unless they are preceded by a proline.

"Exopeptidase enzyme" or "exoprotease" means a proteolytic enzyme capable of breaking peptide bonds at the N-terminus or C-terminus of a peptide and/or protein. These are referred to as aminopeptidase or carboxypeptidase respectively. Exopeptidases allow the generation of monomers, i.e. free amino acids, in the hydrolysate.

According to a particularly preferred embodiment, the protein hydrolysate of the invention is obtained by an enzymatic hydrolysis process comprising the steps of:

a. provision of a protein source;
b. grinding of said protein source;
c. optionally, pH adjustment;
d. addition of at least one hydrolysis enzyme;
e. heating;
f. separation;
g. drying.

Depending on the starting protein substrate, the desired degree of hydrolysis, in particular greater than 10%, but also on the specific content of peptides of given sizes, in particular peptides of a size of less than 5000 Da, or less than 2000 Da, or less than 1000 Da or less than 500 Da, the person skilled in the art will know how to adapt the reaction conditions in a specific manner. The enzymatic hydrolysis step requires determining the enzymes to be used and adjusting various parameters such as the enzyme/substrate ratio, hydrolysis time, stirring speed, pH and temperature.

According to a particular mode, in step (a), the protein source is preferably blue fish, especially sardines, preferably at least blue fish heads and most preferably at least sardine heads.

In step (b), grinding of the protein source advantageously results in the appropriate particle size. The grinding should be as fine as possible to favour the action of the enzymes. Ideally, all particles should be close to 5 mm in size, preferably close to 3 mm. The grinding step can be performed using a dry or wet protein source. The grinding step thus requires adjusting the duration and speed according to the instrument used and the dry or wet nature of the material to be ground, which is what the skilled person is capable of doing in the course of his routine work. The addition of water requires adjustment of the speed, duration, and water/solid ratio depending on the instrument to be used, all of which are within the reach of the person skilled in the art. Preferably, some water is added to the protein source. It is preferably equal to 0.1 to 1 times the mass of said protein source and does not exceed this amount.

In one embodiment, the hydrolysis process comprises an optional step of adding antioxidant. This optional addition can take place at various stages of the process, notably before or after grinding (step b) but also before drying (step g). Anti-oxidant means a chemical or natural compound capable of inhibiting oxidation reactions and preventing the formation of free radicals. The person skilled in the art will know how to adapt the nature and the quantity of antioxidant to be used in order to best adapt the hydrolysis reaction, depending in particular on the protein source used.

The optional pH adjustment step (c) allows the pH of the ground protein source to be adjusted as required. It is indeed important that the pH of this ground mass corresponds to the optimal pH for the functioning of said hydrolysis enzyme. The person skilled in the art knows the means of adapting the pH of the said ground mass, in particular by using bases and/or acids adapted to the agri-food processes, in particular a base such as sodium bicarbonate will make it possible to increase the pH of the said ground mass, whereas an acid such as citric acid or acetic acid will make it possible to lower it.

In particular in step (d), the at least one enzyme used contains at least one endoprotease and/or at least one exoprotease, preferably at least one endoprotease, such as for example serine endopeptidase, aspartic acid endopeptidase and/or cysteine endopeptidase, preferably serine endopeptidase. Preferably, the endopeptidase of the invention is an alkaline endopeptidase and preferably an endopeptidase of microbial origin.

According to a preferred embodiment of step (d), the at least one enzyme used contains at least one alkalase, in particular alkalase 2.4 L as illustrated in the examples.

Advantageously, the heating according to step (e) is carried out for 1 to 20 hours, preferably between 2 and 12 hours, at a temperature between 25° C. and 70° C., preferably between 40° C. and 60° C., and preferably around 55° C. As is well known to the person skilled in the art, the heating step may comprise several temperature steps, in particular with a view to deactivating the enzymes by heating, typically between 80° C. and 105° C. for example for 15 to 40 minutes.

In one particular mode, the mixture is pre-filtered on a sieve to remove solid particles (in particular bones).

The reaction medium is then separated, according to step (f), using any suitable known separation technique, such as centrifugation or settling. Preferably, the reaction medium is separated by centrifugation, in particular vertical and/or horizontal centrifugation. The separation step requires adjustment of parameters such as speed, temperature, time and pH, which is a matter of routine application of the general knowledge of the person skilled in the art. This step advantageously allows the recovery of the soluble fraction, containing soluble peptides, phospholipids and DHA/EPA, and the elimination of the insoluble proteins as well as part of the fat, containing mainly neutral lipids, and in particular triglycerides.

The aqueous phase obtained after separation is then dried (step g) using any suitable known drying technique, such as freeze-drying or evaporative drying, including spray drying or desiccation. Optionally, it is possible to carry out a concentration step prior to the drying step. The person skilled in the art will know how to choose the most suitable drying technique and optimise the drying conditions according to the use to be made of the protein hydrolysate of the invention. In particular, the person skilled in the art may choose to use at least one drying medium. The term "drying medium" refers to any conventional compound for carrying out a drying step within the technical scope of the invention. For example, a suitable drying medium may be selected from microbial proteins (e.g., yeasts), dairy proteins (e.g., caseinates), hydrolysed starches (e.g., maltodextrins), modified starches (e.g., octenyl succinate starch), cyclodextrins, gums (e.g., gum arabic), fibers (e.g., cellulose fibers), and combinations thereof.

In particular, it is essential, in order to obtain the protein hydrolysate of the invention, i.e. a hydrolysate rich in peptides, and comprising phospholipids and DHA/EPA, (1) to carry out a protein hydrolysis with a degree of hydrolysis of at least 10%, and (2) to carry out a phase separation.

In a particular embodiment, the enzymatic hydrolysis process further comprises a DHA supplementation step. The protein hydrolysate of the invention is then obtained by an enzymatic hydrolysis process comprising the steps of:

a. provision of a protein source;
b. grinding of said protein source;
c. optionally, pH adjustment;
d. addition of at least one hydrolysis enzyme;
e. heating;
f. separation;
f. addition of DHA;
g. drying.

In an alternative embodiment, the DHA addition step (step (f')) is performed after the drying step (g). DHA can be either "pure" DHA or an ingredient containing significant amounts of DHA. As a non-limiting example, said ingredient containing a significant amount of DHA may be krill oil.

Another aspect of this invention thus relates to a preparation process of a protein hydrolysate according to the invention comprising the steps of:

a. provision of a protein source;
b. grinding of said protein source;
c. optionally, pH adjustment;
d. addition of at least one hydrolysis enzyme;
e. heating;
f. separation;
g. drying.

In a particular embodiment, this process further comprises a step of adding antioxidant, which can be performed in particular before or after the grinding step (b), or before the drying step (g).

In another particular embodiment, this process further comprises a DHA supplementation step (f') which is performed after the separation step (f) and before the drying step (g). In an alternative embodiment, this process comprises a DHA supplementation step (g') which is performed after the drying step (g).

In another particular embodiment, this process further comprises an antioxidant addition step and a DHA supplementation step. Said antioxidant addition step may in particular be performed before or after the grinding step (b), or before the drying step (g); and said DHA supplementation step may be performed after the separation step (f) and before the drying step (g), or performed after the drying step (g).

Food and/or Pharmaceutical Composition

The protein hydrolysate of the invention (also referred to here as pure hydrolysate powder) is therefore a peptide-rich hydrolysate, and contains phospholipids, DHA and EPA. Thus, when administered in sufficient quantities, the hydrolysate of the invention advantageously provides health benefits.

Food Composition

According to another aspect, the invention relates to a food composition comprising at least one protein hydrolysate according to the invention and as defined above, characterised in that it is a complete food or a food supplement, in particular a functional food or nutraceutical.

According to a first preferred embodiment, the food composition of the invention is a food supplement, in particular a functional food or nutraceutical for humans.

"Human" means a human being, male or female, preferably an adult, in particular an elderly person, at risk of developing age-related cognitive disorders.

Advantageously, the subject is distinguished according to the therapeutic or prophylactic use of the said food composition. Thus, in the context of therapeutic use, said subject is an adult preferably aged 60 years or over. For prophylactic use, particularly to prevent the risk of cognitive decline, the subject is an adult, preferably at least 50 years of age or older.

The term "food supplement" refers to a product that is intended to be ingested in addition to the normal diet. In particular, it is a composition concentrated in nutrients, in particular peptides, phospholipids, DHA, vitamins and/or minerals, which comprises substances with nutritional or physiological purposes. "Functional food" means a food that is similar in appearance to conventional foods, is part of the normal diet, and provides demonstrated physiological benefits and/or reduces the risk of chronic disease beyond basic nutritional functions. A "nutraceutical food" is a food in pill, powder or other medicinal form that is not usually associated with food. The nutraceutical food has a beneficial physiological effect or protects against chronic diseases.

According to this embodiment, said food composition comprising at least one protein hydrolysate according to the invention is intended to be consumed orally. It can therefore be drunk and/or ingested. Advantageously, the food composition of the invention may be in the form of a powder. Said food composition in powder form can thus be packaged in capsules, in particular capsules to be dissolved and/or swallowed.

Thus, said protein hydrolysate is present in the food composition of the invention in an amount sufficient to allow, on a daily dose basis, a daily intake of said hydrolysate ranging from 0.2 grams (gr) to 7 gr, preferably from 0.2 gr to 3 gr and more preferably from 0.5 gr to 3 gr. These doses are given as an indication for a human weighing 60 kg. The person skilled in the art will know how to adapt these doses according to the age and/or weight and/or diet and/or general health status of the subject.

A further object of the invention relates to a food product characterised in that it comprises as an ingredient a food composition as defined above.

Thus, in a particularly advantageous embodiment, the composition of the invention may be incorporated into foods and/or beverages. By way of a non-limiting example, the composition of the invention may be incorporated during the preparation of fruit and/or vegetable juices, fermented or non-fermented dairy products, such as yoghurt or yoghurt drinks, cheeses, but also ice creams; it may also be incorporated during the preparation of biscuits, food bars, lozenges, pastilles, sweets or chewing gum, etc.

According to a second preferred embodiment, the food composition of the invention is a pet food, preferably a dog or cat food.

According to this embodiment, the pet food composition is preferably a complete food.

The terms "pet", "domestic animal" and "animal" are synonymous and refer to any domesticated animal including, but not limited to, cats, dogs, rabbits, guinea pigs, ferrets, hamsters, mice, gerbils, birds, horses, cows, goats, sheep, donkeys, pigs and the like, and preferably cats or dogs. Preferably, the animal is an adult, especially an older one, and at risk of developing age-related cognitive disorders. In a particular embodiment, the animal is a dog, preferably older than 6 years, more preferably older than 7 years.

"Pet food" means any food that may be in any form, solid, dry, moist, semi-moist or combinations thereof. Treats are included in pet food.

"Complete food" means a food that contains all known nutrients required for the intended recipient or consumer of the feed, in appropriate amounts and proportions based on, for example, recommendations from recognised or competent authorities in the field of the considered pet (species/breed/type/age/ . . . ). These foods are the only source of nutritional intake to meet the needs of pets, without the addition of supplementary food sources. Nutritionally balanced pet foods are widely known and used in the art.

There are three main categories or classes of complete pet food, depending on whether the moisture content is low, medium or high:

- dry or low moisture products (with less than about 14% moisture), such as kibbles; these are generally highly nutritious, can be packed in e.g. bags or boxes and are highly suitable for storage and use;
- products in cans or pouches or wet or high moisture content (having more than about 50% moisture), such as "chunky X-products": usually high meat content products;
- semi-wet or semi-dry or dry and tender or wet and tender products or products with a medium or intermediate moisture content (having about 14% to about 50% moisture), such as pâtée: usually packed in appropriate bags or boxes.

The term "kibble" as used here refers to particulate fragments or pieces formed by an agglomeration or extrusion process. Usually, kibbles are produced to give a dry, semi-moist pet food, preferably a dry pet food. Pieces may vary in size and shape depending on the process or equipment. For example, kibbles can be spherical, cylindrical, oval or similarly shaped. They may have a maximum dimension of less than about 2 cm for example.

The term "chunky X-products" is used herein to refer to all edible foods comprising chunks in a preparation (said preparation being "Preparation X"). Classic examples of these are products with chunks in jelly, products with pieces in sauce, and others. This category of "chunky X-products" also includes edible forms other than chunks that may be contained in preparation X such as jelly, sauce, and the like. For example, other forms than chunks can be sliced products, shredded products, etc.

The term "pâtée" as used here refers to edible foods obtained in the form of wet products and includes terrines, pates, mousses, and others.

The term "treat" (or "biscuit") refers to any food that is designed to be given by its owner to a pet, preferably at a time other than mealtimes, to contribute to, promote or maintain a bonding process between a pet and its owner. Sweets or biscuits are not usually suitable for providing 'complete nutrition'. Examples of dog treats are bones. Examples of cat treats are chewable pads and chewable sticks.

In particular, the protein hydrolysate of the invention may be added to said pet food composition by coating or by inclusion, preferably by inclusion.

"Coating" means topical deposition of the hydrolysate of the invention, i.e. deposition on the surface of the pet food, e.g. by spraying, atomisation, etc. The protein hydrolysate of the invention can be added to a pet food by coating, usually in a mixture with one or more palatability enhancers and/or fat.

The term "inclusion" as used herein refers to the addition of the hydrolysate of the invention into the core of the pet food. For example, the inclusion of said hydrolysate in a pet food can be achieved by mixing it with other pet food ingredients, prior to further processing steps, to obtain the final pet food product (including heat treatment and/or extrusion and/or autoclaving, etc.).

In particular, the food comprises between 0.1% and 20%, preferably between 0.1% and 10% by weight of said hydrolysate.

According to this embodiment, the protein hydrolysate is present in a food in an amount sufficient to provide an amount of peptides (water-soluble proteins with a molecular weight of less than 1000 Da) of between 0.05 g and 10 g/100 g of food, in particular between 0.05 g and 5 g/100 g of food.

The said protein hydrolysate is also present in the food composition of the invention in an amount sufficient to provide an amount of phospholipids of between 0.25 mg and 200 mg/100 g food, in particular between 0.25 mg and 150 mg/100 g food.

The said protein hydrolysate is also present in the food composition of the invention in an amount sufficient to provide an amount of DHA and EPA of between 0.5 mg and 150 mg/100 g food, in particular between 0.5 mg and 100 mg/100 g food.

Thus, said protein hydrolysate is present in the feed composition of the invention in an amount sufficient to allow, on a daily dose basis, a daily intake of said hydrolysate ranging from 0.02 grams (gr) to 2 gr, preferably from 0.02 gr to 1 gr per kilo of live weight of the animal.

Another aspect of the present invention concerns a kit comprising, in a single package, several containers:

a) at least one protein hydrolysate as defined above;

b) at least DHA.

According to a particular embodiment of the invention, said kit further comprises:

c) one or more pet food ingredients, preferably selected from the group consisting of proteins, peptides, amino acids, cereals, carbohydrates, fats or lipids, nutrients, palatability enhancers, animal digestates, meat meal, gluten, preservatives, surfactants, texturing, stabilising or colouring agents, inorganic phosphate compounds, flavourings and/or seasoning.

According to another embodiment of the invention, said kit comprises, in a single package, several containers:

a) at least one protein hydrolysate as defined above;
b) one or more pet food ingredients, preferably selected from the group consisting of proteins, peptides, amino acids, cereals, carbohydrates, fats or lipids, nutrients, palatability enhancers, animal digestates, meat meal, gluten, preservatives, surfactants, texturing, stabilising or colouring agents, inorganic phosphate compounds, flavourings and/or seasoning.
c) optionally at least DHA.

Particular kits according to the present invention further comprise means for communicating information or instructions, to assist in the use of the kit items. Said means of communicating information or instructions are therefore an optional part of the kit.

"Containers" include, but are not limited to, bags, boxes, cartons, bottles, wrappings of any kind or shape or material, overwraps, shrink wrappings, stacked or otherwise secured components or combinations thereof, which are used to store materials.

The term "single package" or "one package" means that the components of a kit are physically associated in or with one or more containers and are considered a unit for manufacture, distribution, sale or use. A single package may consist of containers of individual components physically associated so that they are considered a unit for manufacture, distribution, sale or use.

As used herein, the term "means of communicating information or instructions" is a kit component in any form suitable for providing information, instructions, recommendations, and/or guarantees, etc. Such means may include a document, a digital storage medium, an optical storage medium, an audio presentation, a visual display containing information. The means of communication can be displayed on a website, a brochure, a product label, a packaging leaflet, an advertisement, a visual display, etc.

Pharmaceutical Composition

According to another aspect, the invention relates to a pharmaceutical composition comprising at least one protein hydrolysate according to the invention, and as defined above, a pharmaceutically acceptable vehicle and/or an excipient.

The pharmaceutical composition of the invention can be administered systemically, for example, orally, parenterally and in some cases even transdermally. Each of these forms of administration will be more or less adapted to the actual situation of the subject needing the treatment.

"Subject" means a mammal, human or animal, preferably human or pet, preferably human, dog or cat, male or female, preferably elderly and at risk of developing age-related cognitive impairment.

In a preferred embodiment, the pharmaceutical composition of the invention is administered orally.

In a preferred embodiment, the pharmaceutical composition of the invention is in the form of a powder comprising at least one protein hydrolysate according to the invention.

In the form of a powder, the pharmaceutical composition of the invention may be packaged as hard or soft capsules, lozenges, sachets, tablets, especially soluble or effervescent tablets for oral administration.

In a preferred embodiment, the pharmaceutical composition of the invention is packaged as hard of soft capsules to be swallowed.

In another preferred embodiment, the pharmaceutical composition of the invention is packaged in sachets as a powder to be dissolved.

The present invention further relates to products comprising a protein hydrolysate according to the invention and DHA as a combination product for simultaneous, separate or staggered use as a medicine.

Such a combination product may, according to other embodiments, be used in particular as a neuroprotective agent and/or to prevent and/or treat neuroinflammation and/or in the treatment or prevention of age-related mild cognitive disorders and/or to prevent and/or limit anxiety disorders and/or to prevent and/or limit stress and/or to prevent and/or treat memory disorders and/or to improve and/or promote spatial learning, preferably related to ageing.

In the context of the present invention, the term "simultaneous administration" means that the protein hydrolysate and DHA are administered together in one single pharmaceutical and/or food composition.

In the context of the present invention, the term "separate administration" means that the protein hydrolysate and the DHA are administered at the same time by means of two or more separate pharmaceutical and/or food compositions.

In the context of the present invention, the term "staggered" means that the protein hydrolysate and DHA are administered successively by means of two or more separate pharmaceutical and/or food compositions.

When the protein hydrolysate and DHA are administered sequentially, they may be administered within a time interval of 0 to 120 minutes, especially 0 to 60 minutes, preferably 0 to 30 minutes and most preferably 0 to 5 minutes.

Therapeutic Use

Surprisingly, the inventors were able to demonstrate that the protein hydrolysate according to the invention (or pure hydrolysate in powder form), as described above, has protective virtues against age-related mild cognitive disorders, in particular to prevent and/or limit anxiety disorders, to prevent and/or limit stress, to prevent and/or treat memory disorders, and to improve and/or promote spatial learning. Thus, the inventors were able to show that the protein hydrolysate of the invention had in particular a neuroprotective effect and an anti-neuroinflammatory effect.

Thus, another object of the invention relates to a protein hydrolysate according to the invention or a pharmaceutical composition containing it, for use as a medicinal product.

Such a use as a medicinal product may be, preferably age-related, a use as a neuroprotective agent and/or a use in preventing and/or treating neuroinflammation and/or a use in the treatment or prevention of age-related mild cognitive disorders and/or a use in preventing and/or limiting anxiety disorders and/or preventing and/or limiting stress and/or preventing and/or treating memory disorders and/or improving and/or promoting spatial learning, preferably age-related disorders.

The invention further relates to a protein hydrolysate according to the invention or a pharmaceutical composition containing it, for use as a neuroprotective agent.

The invention also relates to a protein hydrolysate according to the invention or pharmaceutical composition containing it, for use in preventing and/or treating neuroinflammation.

The invention also relates to a protein hydrolysate according to the invention or a pharmaceutical composition containing it, for use in the treatment or prevention of mild age-related cognitive disorders.

The invention also relates to a protein hydrolysate according to the invention or pharmaceutical composition containing it, for use in preventing and/or treating age-related disorders, preventing and/or limiting anxiety disorders, preventing and/or limiting stress, preventing and/or treating memory disorders, improving and/or promoting spatial learning.

The term "medicinal product" as used herein refers to both a product for human use and a veterinary product for use in pets. The drug can be administered in very different ways depending on its mode of action and its ability to be absorbed by the subject to whom it is administered. A drug can therefore be administered, for example, topically in the form of spot-on formulations, as shampoos, showers, dips, baths or sprays, as animal collars and in many variations of these forms of application. It can also be administered systemically, for example, orally, parenterally and in some cases even transdermally. Each of these forms of administration will be more or less adapted to the actual situation and to the pet or human needing the treatment.

"Treatment" means reducing age-related mild cognitive impairment. Such a reduction can be demonstrated through analysis showing a reduction in anxiety disorders, and/or stress, and/or memory disorders and/or an improvement in spatial learning. Advantageously, the treatment completely eliminates age-related mild cognitive impairment, but the term "treatment" includes any significant reduction in such impairment. In the context of the treatment of mild age-related cognitive disorders, the composition according to the invention may be combined with another usual treatment for mild age-related cognitive disorders well known to the person skilled in the art.

Prophylaxis means reducing the likelihood of age-related mild cognitive impairment. However, the term "prophylaxis" also covers the possibility of significantly decreasing the frequency of occurrence of mild age-related cognitive impairment in a population of subjects ingesting an effective amount of the protein hydrolysate according to the invention during the time of intake, as compared to a population of similar subjects not taking the protein hydrolysate according to the invention (in which case the likelihood of mild age-related cognitive impairment during intake of the protein hydrolysate of the invention is merely significantly decreased). For such a comparison, the populations being compared should be similar, especially with regard to the proportion of subjects at risk of age-related mild cognitive impairment.

Thus, the oral administration of the compositions of the invention is particularly advantageous in the case of prophylaxis of mild age-related cognitive disorders. Indeed, regular oral administration of the hydrolysate of the invention makes it possible to prevent inflammation and then to maintain a low level of inflammation in microglial and neuronal cells in the long term, particularly in the hippocampus.

The invention further relates to the use of a protein hydrolysate, or a pharmaceutical composition containing it, for the manufacture of a medicinal product for the treatment or prophylaxis of mild age-related cognitive impairment.

Advantageously, said protein hydrolysate is as described above.

The invention further relates to a method of prophylactically or therapeutically treating mild age-related cognitive impairment comprising administering to a subject in need thereof an effective amount of a protein hydrolysate, or a pharmaceutical composition containing the same.

The invention further relates to a method of prophylactically or therapeutically treating mild age-related cognitive impairment comprising the simultaneous, separate or timed administration to a subject in need thereof of an effective amount of products containing a protein hydrolysate and DHA, as a combination product.

In the present treatment method, said protein hydrolysate is as described above.

An "effective amount" of a protein hydrolysate or pharmaceutical composition containing it, as used herein, is an amount of the protein hydrolysate or pharmaceutical composition containing it provided by a particular route of administration and according to a particular mode of administration, which is sufficient to achieve a desired therapeutic and/or prophylactic effect as defined above. The amount of protein hydrolysate or pharmaceutical composition containing it administered to the subject will depend on the type and severity of the disease, the type, age, body weight, general health, gender and diet of the subject; the time of administration, route of administration and rate of elimination of the specific compound employed; the duration of treatment; drugs used in combination or concomitantly with the hydrolysate or pharmaceutical composition containing it; and similar factors well known in the medical art. The person skilled in the art will know how to determine the appropriate dosages according to these and other factors. For example, it is well known to the person skilled in the art to start with doses of the compound at levels below those required to achieve the desired therapeutic and/or prophylactic effect and to progressively increase the dosage until the desired effect is achieved.

The present invention will be described in detail with reference to the following examples, which are for illustrative purposes only and are not intended to limit the scope of the invention.

EXAMPLES

The hydrolysates illustrated below in accordance with the present invention are pure powdered hydrolysates as described above.

Example 1: Equipment and Methods 1.1. Cell Cultures

BV2:

BV2 cells are derived from a neonatal murine microglial cell line immortalized by the raf/mycet system, provided by Dr. Watterson (NorthWestern University, USA). They were grown in complete medium containing RPMI-Glutamax with 2 mM glutamine (Invitrogen, Life Technologies, France) supplemented with 10% inactivated fetal calf serum and 1% penicillin (100 U/mL)-streptomycin (100 μg/mL; Sigma-Aldrich, France) under a humid atmosphere with 5% CO2 at 37° C. as described by De Smedt-Peyrusse et al. (8).

When the cells had reached 80% to 90% confluence, they were treated for 24 hours with:

- DHA at the concentration of 16 μM (Sigma-Aldrich, France). This concentration of DHA has been validated in the laboratory as an effective dose to demonstrate an anti-inflammatory effect.

the hydrolysate according to the invention providing 16 μM of DHA.

The cells were then treated for 2 h, 6 h or 24 h with 1 μg/mL of LPS (lipopolysaccharides) (Sigma-Aldrich) to induce inflammatory stress and then collected in Trizol (n=6; Invitrogen, Life Technologies).

Co-Culture:

In order to have a more complex model, a so-called "sandwich" co-culture was performed between neuronal cells (HT22) and microglial cells (BV2). In a first step, the two cell types are cultured separately. The HT22 cells are derived from a mouse hippocampal cell line, provided by Dr. E. Maronde (Germany). They were grown in complete medium containing DMEM (Invitrogen, Life Technologies) supplemented with 10% inactivated fetal calf serum and 1% penicillin (100 U/mL)-streptomycin (100 μg/mL; Sigma-Aldrich) in a humid atmosphere with 5% CO2 at 37° C.

BV2 were cultured in RPMI complete medium in simple 6-well plates and HT22 in DMEM complete medium on cover slips. After 24 hours of culture, the HT22s were returned to the microglial mat in order to treat both cell lines for 16 hours with the hydrolysate according to the invention providing 16 μM of DHA.

The cells were then treated for 6 h with 1 μg/mL LPS to induce inflammatory stress and collected separately (n=5).

1.2. Animals and Treatments

All experiments were conducted on 7-week-old and 12-month-old male C57Bl/6J (January) mice.

The mice were placed in individual cages to monitor their food intake and weight gain. For 12 weeks, they were fed ad libitum with an n-3 PUFA-deficient diet that mimicked age-related n-3 PUFA deficiencies. At the end of this period, the animals were supplemented with the hydrolysate.

For the H1 hydrolysate, the animals were divided into 4 groups, supplemented or not:

Young Control (n=12), receiving the n-3 PUFA deficient diet.

Aged Control (n=12), receiving the n-3 PUFA deficient diet.

Young H1 (n=12), receiving the H1 hydrolysate according to the invention.

Aged H1 (n=12), receiving the H1 hydrolysate according to the invention.

TABLE 1

| H1 hydrolysate | | |
|---|---|---|
| g/kg of diet | Control Diet | H1 Diet |
| H1 hydrolysate according to the invention | — | 200 |
| Peptides | — | 140 |
| DHA | — | 3.05 |

For the H2 hydrolysate, the animals were divided into 6 groups, supplemented or not:

Young Control (n=12), receiving the n-3 PUFA deficient diet.

Aged Control (n=13), receiving the n-3 PUFA deficient diet.

Young H2 (n=12), receiving the H2 hydrolysate according to the invention.

Aged H2 (n=13), receiving the H2 hydrolysate according to the invention.

Young H2+DHA (n=12), receiving the H2 hydrolysate according to the invention enriched with DHA.

Aged H2+DHA (n=13), receiving the H2 hydrolysate according to the invention enriched with DHA.

TABLE 2

| H2 hydrolysate | | | |
|---|---|---|---|
| g/kg of diet | Control Diet | H2 Diet | H2 + DHA diet |
| H2 hydrolysate according to the invention | — | 1.66 | 1.66 |
| Peptides | — | 1.11 | 1.11 |
| DHA | — | 0.029 | 0.0352 |
| DHA (Polaris) | — | — | 2 |

After 6 weeks of supplementation, all the mice were subjected to behavioural tests assessing their cognitive abilities and their reactivity to stress. At the end of these protocols, the animals were euthanised and the structures of interest, including the hippocampus, were harvested. The effect of supplementation on the expression of inflammatory and neurotrophic factors was determined by real-time quantitative PCR.

The acute inflammation study was conducted in 7-week-old male C57Bl/6J (January) mice.

The mice were placed in groups of 6 in collective cages, with ad libitum access to water and a standard diet (A04 diet, Safe, Augy, France) and then gavaged for 18 days via a gastric tube (Ecimed, Boissy-Saint-Léger, France). The mice were divided into 3 groups, supplemented or not:

Control (n=11), receiving 100 μL water+50 μL peanut oil

H2 (n=10), receiving 100 μL of H2 hydrolysate+50 μL of peanut oil

DHA (n=12), receiving 100 μL water+50 μL DHA (Polaris, Quimper, France)

TABLE 3

| H2 hydrolysate gavage | | | |
|---|---|---|---|
| | Control | H2 | DHA |
| Water (μL/day) | 100 | — | 100 |
| Peanut oil (μL/day) | 50 | 50 | — |
| H2 hydrolysate according to the invention (μL/day) | — | 100 | — |
| Peptides (mg/day) | — | 5.5 | — |
| DHA (mg/day) | — | 0.143 | — |
| DHA (μL/day)(10 mg/day *) | — | — | 50 |

* proven effective dose for cognition effect

After 18 days of supplementation, mice were injected intraperitoneally with 125 μg/kg of LPS (*Escherichia coli,* 0127: B8, Sigma-Aldrich, Lyon, France) (Rey et al., 2019 (9); Mingam et al., 2008 (10)) in order to induce an inflammatory reaction or injection of a saline solution (0.9% NaCl). Two hours after injection, the mice were euthanised and the structures of interest, including the hippocampus, were harvested.

1.3. Behavioural Tests 1.3.1. Y-Maze:

6 weeks after the start of supplementation, hippocampal-dependent spatial recognition memory was assessed using the Y-maze as described by Labrousse et al. (11) and Moranis et al. (12). This hippocampal-dependent spatial memory test is based on the rodents' curiosity and their ability to distinguish a new environment from a familiar one. It thus allows an evaluation of the spatial memory linked to the hippocampus. This test is performed in a Y-shaped maze with 3 arms (35 cm long and 10 cm deep), illuminated at 15 lux. Visual cues are placed on the walls, allowing the mice to find their way within the space.

First, the animal is placed in a starting arm and faces the other two arms, one of which is closed. It has 5 minutes to explore the two open arms and is then placed back in its cage for 1 hour. During the restitution phase, the animal is again placed in the maze for 5 minutes, but this time with all 3 arms open. Due to their strong exploratory behaviour, animals will preferentially explore the new arm. Animals randomly exploring all 3 arms have impaired memory abilities.

The animals are filmed and videotracked (SMART software, Bioseb) in order to analyse the time spent (minutes) in the different arms. In addition, a recognition index was calculated to compare the performance of the animals against chance (33%): time spent in the new arm/(time spent in the new arm+time spent in the familiar arm+time spent in the starting arm).

1.3.2. "Open-Field":

7 weeks after the start of the supplementation, the anxiety-like behaviour of the animals was assessed using the "Open-Field" test. This test is based on the aversion produced by an unknown and open environment. The test is performed using an opaque device (25 cm wide, 45 cm long and 40 cm deep) illuminated at 30 lux. The device is virtually divided in two parts: the central part considered as anxiety-provoking, and the peripheral part considered as less anxiety-provoking. The animals are free to explore the open field for 10 minutes, they are filmed and videotracked (SMART software, Bioseb) in order to measure the time spent (minutes) in the different areas.

1.3.3. Morris' Water Maze:

7 weeks after the start of supplementation, learning and spatial memory abilities were assessed using the Morris water maze (13). The experimental protocol used for this study specifically involves hippocampal-dependent spatial reference memory.

The protocol used is that described by Bensalem et al. (14). It consists of 4 phases:

- Familiarisation: allows mice to become familiar with swimming and then climbing on a platform in a basin (60 cm diameter), for 2 days (days 1 and 2).
- Indexed learning: carried out on the 3rd day, it allows the assessment of motor and visual deficits and the accentuation of familiarisation. The animals must find a marked underwater platform.
- Spatial reference learning: animals must learn to find the non-visible submerged platform using visual spatial cues (days 4-7). To this end, the mice have 6 trials/day (cut-off of 90 s) for 4 consecutive days. The swimming speed, latency to reach the platform, distance and path covered by the animals for each trial were recorded by a video-tracking system (Imetronic).

1.3.4. The Probe Test:

This test assesses spatial memory. 72 hours after the last day of training, the platform is removed from the pool and the animal is placed in the pool for 60 seconds. The animals were videotracked (SMART software, Bioseb) in order to measure the time spent (seconds) and the distance covered (cm) in the "target" quadrant, i.e. the quadrant where the platform was located during the spatial learning phase.

1.3.5. Analysis of Learning Strategies:

For each trial during spatial learning, the swimming trajectories were analysed using the replay of the Imetronic videotracking software. The platform search strategies were blindly classified and then assigned for each trial using a classification scheme similar to those previously developed for other studies (15, 16, 17). These strategies are divided into two main categories: non-spatial and spatial strategies.

The non-spatial strategies consist first of "global search" strategies: "peripheral search" (the animal swims preferentially in a 15 cm zone around the edges of the pool), "random search" (search in the whole pool covering >75% of the surface), "circle search" (the mouse makes very small circles and can make some sharp movements in given directions). Then there are "local search" strategies: the "sweep" (the animal searches in a limited area, often in the centre, of the pool covering between 15 and 75% of the surface), the "loop" (the mouse swims in a circular fashion at a fairly fixed distance, greater than 15 cm, from the edges), the "repeated incorrect" (the animal swims in a precise direction that does not correspond to the position of the platform and repeats the same trajectory several times), and finally the "incorrect focus" (the animal searches intensively in a small portion of the pool that does not contain the platform).

Spatial strategies include 'repeated correct' (where the animal swims in the direction of the platform and then repeats the same trajectory several times), 'indirect spatial' (the animal swims indirectly towards the platform, possibly making one or two loops), 'direct spatial' (the mouse swims directly towards the platform), and 'focus correct' (the animal swims and then searches intensively in the quadrant where the platform is located).

1.3.6. Reactivity to Stress:

Stress reactivity was assessed 10 weeks after the start of supplementation. To this end, the animals are subjected to a 30-minute restraint test. A cheek blood sample is taken from the mandibular vein at the start of the test (TO), then 30 minutes (T30) and 60 minutes (T60) after the start of the test. The mice are euthanised 90 minutes (T90) after the test and an intracardiac puncture is performed to obtain a blood sample.

1.4. Biochemical Analyses 1.4.1. Measurement of Plasma Corticosterone Levels:

Plasma was isolated from blood by centrifugation at 3000 g for 20 minutes. From the plasma, a determination of total corticosterone was carried out using the ELISA DetectX® "Corticosterone, Enzyme Immunoassay Kit" according to the supplier's instructions (Arbor Assay). The corticosterone concentration (ng/mL) of each sample is calculated based on the spectrophotometric standard.

1.4.2. Gene Expression:

The expression of the different genes of interest was assessed by real-time quantitative PCR as described by Rey et al. (18). These analyses were performed on BV2 and HT22 cells and on the hippocampi.

1.4.3. Extraction of Total RNA:

Total RNA was extracted from cells and hippocampi using the TRIzol reagent extraction protocol (Invitrogen, Life Technologies) containing phenol and guanidine isothiocyanate.

This reagent allows, after lysis and addition of chloroform, to separate an upper aqueous phase containing RNA from an organic phase containing DNA and proteins. After recovery of the aqueous phase, the RNA is precipitated with glycogen (20 mg/mL) and isopropanol. After successive washes with 70% ethanol, the RNA pellet is dried and then recovered in 10 μL of sterile water. The purity and amount of RNA in each sample was measured spectrophotometrically (Nanodrop, Life technologies).

1.4.4. Reverse Transcription:

Reverse transcription (RT) was performed with 1 μg or 2 μg of RNA, depending on the amount obtained, to synthesise complementary DNA (cDNA). RNAs were incubated at 37°

C. for 15 minutes and then at 75° C. for 1 minute with a mixture of DNAse buffer, RNAsin, DNAse I (Invitrogen, Life Technologies). A second incubation at 65° C. for 5 minutes in the presence of random primers (150 ng/μL, Invitrogen) and 10 mM dNTP is performed. Finally, a mixture of 5× buffer, DTT, RNase OUT at 40 U/μL and Supercript III at 200 U/μL (Invitrogen, Life Technologies) is added. The reaction mix is incubated at 25° C. for 5 minutes, then 50° C. for 50 minutes and 70° C. for 15 minutes. The final concentration of cDNAs obtained is 50 ng/μL (if 1 μg of initial RNA) or 100 ng/μL (if 2 μg of initial RNA).

1.4.5. Real-Time Quantitative PCR:

The cDNAs from the RT reaction were selectively amplified using primers specific to the sequences of the target genes under investigation. The reference gene used here is β-Actin, and the target genes studied for co-culture are: IL-6, IL-1β, TNF-α, BDNF and NGF.

For the study of chronic inflammation, the following target genes were amplified: in the hippocampus IL-6, IL-1β, TNF-α, CD11 b and Iba1, and in the hypothalamus: CrhR1, CRHBP, HSD11b1. For the study of acute inflammation, the following target genes were amplified for hippocampi: IL-6, IL-1β, TNF-α, COX-2, BDNF and NGF.

For each sample, 2 μl of cDNA at 20 ng/μl was added to 8 μl of a mixture comprising Taq polymerase (5×), target gene oligonucleotide pairs (2×) and sterile water (1×). The plate was then placed in a Light Cycler thermocycler (LC 480 version 2, Roche) in order to perform the PCR programme: an activation phase (2 minutes at 95° C.) and 50 amplification cycles, each comprising a denaturation phase (15 seconds at 95° C.), and an oligonucleotide hybridisation and elongation phase (1 minute at 60° C.).

The final quantification was performed using the comparative Cycle Threshold (Ct) method. For each target gene and each sample, the transcript level was normalized with the transcript level of the reference gene (β-Actin).

1.4.6. Biomark Card

RT cDNAs were diluted (1.3 μL, 5 ng/μL) and then added to DNA Binding Dye Sample Loading Reagent (Fluidigm), EvaGreen (Interchim, Montluçon, France) and low-EDTA Tris-EDTA (TE) buffer to form the sample plate. In the Mix plate, 10 μL of primer pairs (100 μM) were added to the assay loading reagent (Fluidigm) and low EDTA TE buffer to give a final concentration of 5 μM. After the chip was activated in the integrated fluidic circuit controller, the sample mixture (5 μL) and the test mixture (5 μL) were loaded into the sample inlet wells. One of the wells was filled with water as a check for contamination. To verify the amplification of specific targets and the efficiency of the quantitative polymerase chain reaction (qPCR) process, a control sample (mouse gDNA, ThermoFisher, Waltham, USA) was processed, pre-amplified and quantified in a control assay (RNasePTaqMan probe, ThermoFisher) using the same process in the same plate at the same time. The chip was inserted into the IFC controller, into which 6.3 nL of sample mix and 0.7 nL of Mix were mixed. Real-time PCR was performed using the biomarker system (Fluidigm) on the GenoToul platform (Toulouse, France) with the following protocol: Thermal mixing at 50° C., 2 min; 70° C., 30 min; 25° C., 10 min, Uracil-DNA N-glycosylase (UNG) at 50° C., 2 min, hot start at 95° C., 10 min, PCR cycle of 35 cycles at 95° C., 15 s; 60° C., 60 s and melting curves (from 60° C. to 95° C.). The results were analysed using Fluidigm v.4.1.3 real-time PCR analysis software. (San Francisco, USA) to monitor the specific amplification of each primer. Next, the raw qPCR data were analysed using the GenEx software (MultiD analyses AB, Freising, Germany) to select the best reference gene, in this case β-Actin, for mRNA expression normalisation and to measure the relative expression of each of the 46 genes analysed.

1.4.7. Protein Expression

Western blot allows the detection of target proteins using antibodies directed against these proteins. The samples were diluted with RNase-Free water to a concentration of 1 μg/μL in 200 μL. A 50 μL volume of each sample was taken and 12.5 μL of loading buffer was added.

The samples were then heated at 75° C. for 5 minutes to denature the proteins. SDS-PAGE electrophoresis under denaturing conditions only allows the migration of proteins in an electric field according to their molecular weight. The polyacrylamide gel was poured and then coated with a migration buffer which allows the migration of proteins. The samples, together with a size marker, were deposited in the gel wells and migrated at 90V for 30 minutes and 130V for 1 hour. In order to detect the proteins, they were transferred onto nitrocellulose membrane (75V for 1.5 hours with transfer buffer). To check that the transfer was working properly, the membranes were stained with Ponceau red and then rinsed. Non-specific sites were blocked by incubation in 0.05% TBS/Tween-20 (TBST) and 5% milk (Regilait skim milk) for 1 hour to avoid interactions between the membrane and the antibody. After rinsing with TBST, the membranes were incubated overnight at 4° C. in 5% BSA, 1% sodium azide with the following primary antibodies: anti-GAPDH, anti-IκB. After three successive washes with TBST, the membranes were incubated for 1 hour with a rabbit peroxidase-conjugated secondary antibody solution. After five further washes with TBST and TBS, the membranes were incubated for 5 minutes in a peroxidase developer solution (SuperSignal West Dura, ThermoFisher, Waltham, USA). The proteins were then revealed using the ChemiDoc MP apparatus (Biorad, Hercules, USA). The ratio of the intensity of the target protein bands to the reference protein bands (endogenous control, GAPDH) was used to compare the relative expression of the proteins.

1.4.8 Brain Fatty Acid Analysis

The lipids in the cortex were extracted (Folch et al., 1997 (19)) and the fatty acids were transmethylated according to the method of Morrison and Smith (Morrison and Smith, 1964). Fatty acid methyl esters were analysed by gas chromatography on a Hewlett Packard 5890 series II (Palo Alto, CA, USA) equipped with an injector, a flame ionisation detector (Palo Alto, CA, USA), and a CPSIL-88 column (100 m×0.25 mm inner diameter; film thickness, 0.20 μm; Varian, Les Ulis, France). The carrier gas was hydrogen (inlet pressure, 210 kPa). The furnace temperature was held at 60° C. for 5 min, then increased to 165° C. at 15° C./min and held for 1 min, then to 225° C. at 2° C./min and finally held at 225° C. for 17 min. The injector and detector were held at 250° C. and 280° C., respectively. The fatty acid methyl esters were identified by comparison with the standards. The fatty acid composition is expressed as a percentage of total fatty acids.

1.4.9. Quantification of Oxylipins

The different metabolites derived from arachidonic acid (AA), linoleic acid (LA), DHA and EPA were extracted from the hippocampus and analysed by mass spectrometry (LC-MS/MS) at the METATOUL platform (MetaboHUB, INSERM UMR 1048, I2MC, Toulouse, France) as previously described by Le Faouder et al. 2013 (20).

1.5. Statistics

Statistical analyses were performed with GraphPad Prism and Statistica software. For the Open Field, stress reactivity and qPCR analyses, the 6 experimental groups were compared by 2-factor ANOVAs (age and diet) followed by a Tukey's post-hoc test in case of statistically significant interaction between the factors. For the Y-maze the 6 experimental groups were compared by a one sample t-test against the 33% chance value. For the analysis of the Morris water maze, the learning phase of the 6 experimental groups was analysed by a 3-factor repeated measures ANOVA (age, diet and day); and the probe test was analysed by a 1-factor ANOVA (quadrants).

Data were expressed as means±standard deviation from the mean (SEM), and differences were considered significant when the p value was less than 0.05.

1.6. Preparation of the Hydrolysates

A protein hydrolysate, H1, was obtained by the following procedure: an aqueous solution containing 50% sardine head grist was hydrolysed at 55° C. by alkalase 2.4 L, for 2 hours. The enzyme was then inactivated by heating at 95° C. for 30 minutes. Solid particles (bones) were removed by sieving. A vertical centrifugation step was then carried out to remove the sludge and the fatty phase (mainly insoluble proteins, neutral lipids—triglycerides—and mineral matter). The aqueous phase was thus isolated and dried.

A protein hydrolysate, H2, was obtained by the following process: an aqueous solution containing 87% sardine head grist was hydrolysed at 55° C. by alkalase 2.4 L for 3 hours. The enzyme was then inactivated by heating at 95° C. for 30 minutes. Solid particles (bones) were removed by sieving. A vertical centrifugation step was then carried out to remove the sludge and the fatty phase (mainly insoluble proteins, neutral lipids—triglycerides—and mineral matter). The aqueous phase was thus isolated and dried.

1.7. Characterisation of the Hydrolysates

Several characteristics of the H1 and H2 hydrolysates were determined, as shown in Table 4.

The DH was determined by (1) the pH-stat method, as described by J. Adler-Nissen (21), as well as (2) by the OPA method, as described by Nielsen, P (22).

Moisture was measured according to the method of EC Regulation 152/2009.

The amount of total protein was determined by the Dumas method, based on the NF EN ISO 16634-1 standard.

The amount of soluble protein was determined by solubilising the sample in ultrapure water, recovering the aqueous phase after centrifugation and applying the Kjedahl method (EC Regulation 152/2009) on the aqueous phase.

The quantity of mineral matter was determined according to the method of standard NF V04-404—April 2001.

The amount of total fat (or total lipids) was determined according to the method of EC Regulation 152/2009.

The amounts of neutral lipids, including triglycerides, and polar lipids, including phosphatidylcholine, were determined by HPTLC (High-Performance Thin-Layer Chromatography). The different classes of neutral and polar lipids were analysed separately by HPTLC (High performance Thin layer chromatography) on glass plates (10×20 cm) impregnated with silica 60 (Merck). A preliminary wash of the plate was carried out with a mixture of hexane/diethyl ether (97:3, v/v) in the case of neutral lipids, and with a mixture of methyl acetate/isopropanol/chloroform/methanol/KCl (0.25%) (10:10:10:4:3.6; v:v) in the case of polar lipids, in order to remove possible impurities. The plates were then activated at 110° C. for 30 minutes. The lipid extracts were deposited in a suitable quantity according to the samples by an autosampler (CAMAG). Double development allowed the separation of neutral lipids. For the first migration a mixture of hexane/diethyl ether/acetic acid (20/5/0.5, v:v:v) was used and for the second migration a mixture of hexane/diethyl ether (93/3, v:v). Polar lipids were separated after a single development, using a mixture of methyl acetate/isopropanol/chloroform/methanol/KCl (0.25%) (10:10:10:4:3.6; v:v) as elution solvent.

After revelation by immersion of the plates in a solution of cupric acid and phosphoric acid followed by heating to 120° C. for 20 minutes, the different classes of neutral and polar lipids appeared as black spots. Six classes of neutral lipids (alcohols, free fatty acids, sterol esters, glyceride ethers, triacylglycerols and sterols) and 7 classes of polar lipids (phosphatidyl ethanolamine, phosphatidyl choline, phosphatidyl serine, phosphatidyl inositol, cardiolipid, ceramide aminoethylphosphonate and lysophosphatidyl choline) could be separated and identified by comparison with standards. Quantification was performed by external calibration, densitometry using a scanner set at 370 nm and Wincats software (CAMAG).

The amounts of omega 3 and omega 6, DHA and EPA, plasmalogens were determined as described by Mathieu-Resuge, et al. (23).

TABLE 4

Characteristics of H1 and H2 hydrolysates

| | H1 | H2 |
|---|---|---|
| DH (pH-stat) (%) | 16.0 | 12.8 |
| DH (OPA) (%) | 32.2 | 30.3 |
| Moisture (g/100 g) | 2.6 | 3.4 |
| Total protein (g/100 g) | 72.1 | 69.6 |
| Soluble protein (g/100 g) | 70.4 | 67.0 |
| Mineral matter (g/100 g) | 9.5 | 9.0 |
| Total fat (=total lipids) (g/100 g) | 7.8 | 10.3 |
| Phosphatidylcholine (mg/g) | 10.0 | 8.9 |
| Omega 3 (mg/g) | 26.5 | 33.8 |
| Omega 6 (mg/g) | 3.6 | 4.5 |
| DHA (mg/g) | 13.5 | 17.3 |
| EPA (mg/g) | 6.6 | 8.4 |
| Plasmalogens (mg/g) | 0.2 | 0.3 |
| Neutral fat (mg/g) | 61.6 | 85.5 |
| Triglycerides | 58 | 73.6 |
| Polar lipids (mg/g) | 16.4 | 18.2 |
| EPA | 0.9 | 0.9 |
| DHA | 4.9 | 4.4 |

The molecular weight profile of the water-soluble proteins was determined by SEC chromatography as described in F. Guerard et al. (24).

TABLE 5

Molecular weight profile of water-soluble proteins

| | H1 | H2 |
|---|---|---|
| >5000 Da | 0.4 | 0.6 |
| 1000-5000 Da | 10.7 | 12.8 |
| 500-1000 Da | 14.4 | 12.9 |
| <500 Da | 74.5 | 73.7 |

Example 2: In Vitro Effect of the Hydrolysate 2.1. Effect of H1 Hydrolysate on Neuroinflammation of BV2 Microglial Cells Microglial cells are the immunocompetent cells of the brain, responsible for the production of cytokines. Inflammatory stress was induced in these cells (BV2 cells) by liposaccharide (LPS) using the protocol described in Example 1.1. The H1 protein hydrolysate was then tested for its ability to decrease the expression of the pro-inflammatory cytokines IL-6 (interleukin 6), IL-1β (interleukin 1beta) and TNF-α (tumor necrosis factor alpha), in these cells, according to the protocol described in Example 1.4.5.

Figure 1B:
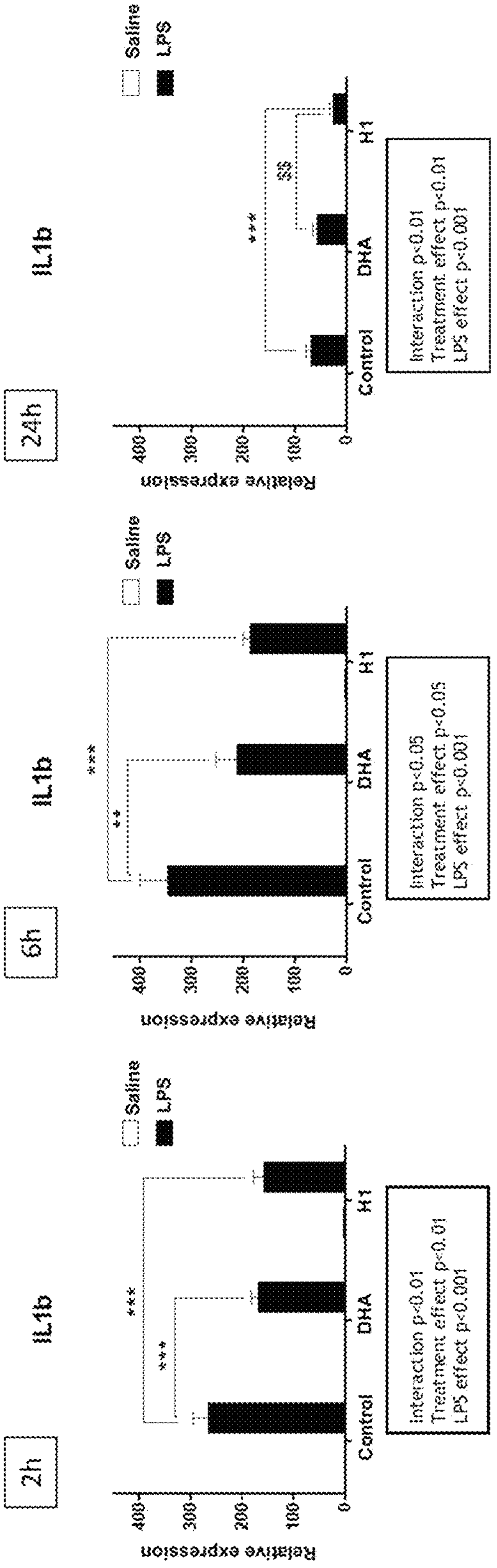
FIG. 1*b*: In vitro effect of H1 hydrolysate or DHA on the expression of the pro-inflammatory cytokine IL-1β in BV2 microglial cells after 2 h, 6 h and 24 h of LPS treatment (n=9; p<0.01, *p<0.001 LPS Control vs LPS Treatment, $p<0.05, $$p<0.01 DHA LPS vs H1 LPS).
Figure 1C:
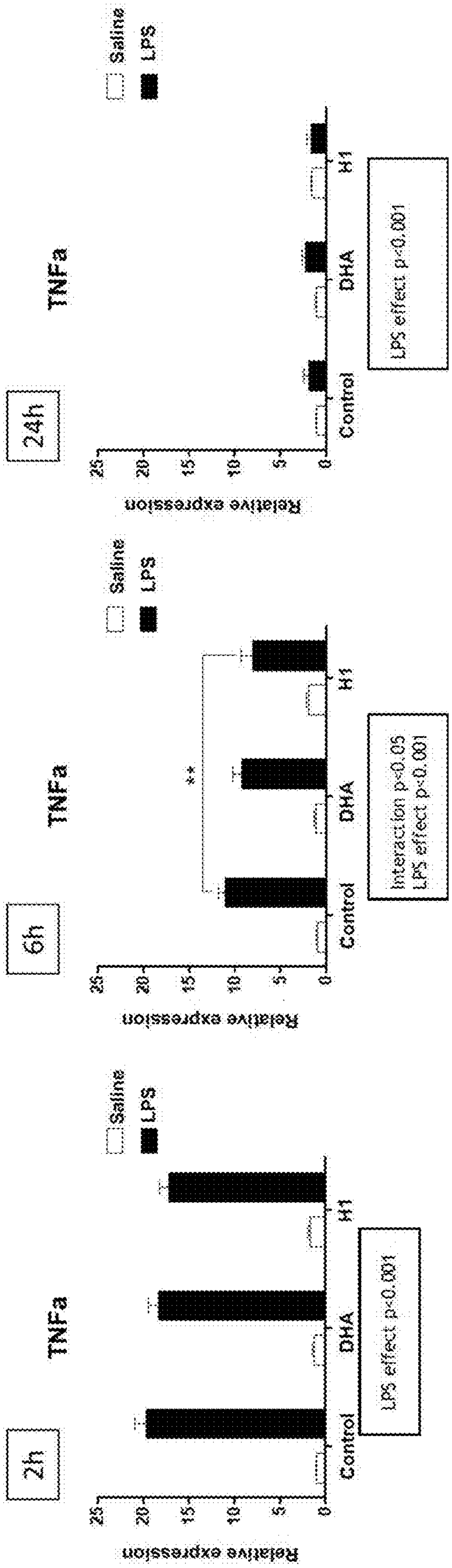
FIG. 1*c*: In vitro effect of H1 hydrolysate or DHA on the expression of the pro-inflammatory cytokine TNF-α in BV2 microglial cells after 2 h, 6 h and 24 h of LPS treatment (n=9; p<0.01, *p<0.001 LPS Control vs LPS Treatment, $p<0.05, $$p<0.01 DHA LPS vs H1 LPS).

The results show that in the control condition, LPS induces inflammatory stress with high expression of IL-6, IL-1β and TNF-α. DHA, which has anti-inflammatory capabilities, reduces LPS-induced IL-6 and IL-1β expression. Surprisingly, treatment with H1 hydrolysate decreases LPS-induced IL-6 and IL-1 expression with a greater effect than DHA (FIGS. 1*a* and 1*b*). The H1 hydrolysate also decreases the expression of TNF-α (FIG. 1*c*).

2.2. Effect of H2 Hydrolysate on Neuroinflammation of BV2 Microglial Cells

In order to mimic a more complex cell interaction system, the H2 hydrolysate was tested in a co-culture system between microglial cells and neuronal cells (BV2-HT22). Inflammatory stress was induced in BV2 microglial cells by liposaccharide (LPS) using the protocol described in Example 1.1. The H2 protein hydrolysate of the invention was then tested for its ability to decrease the expression of the pro-inflammatory cytokines IL-6, IL-1β and TNF-α in these cells, using the protocol described in Example 1.4.5.

Figure 2:
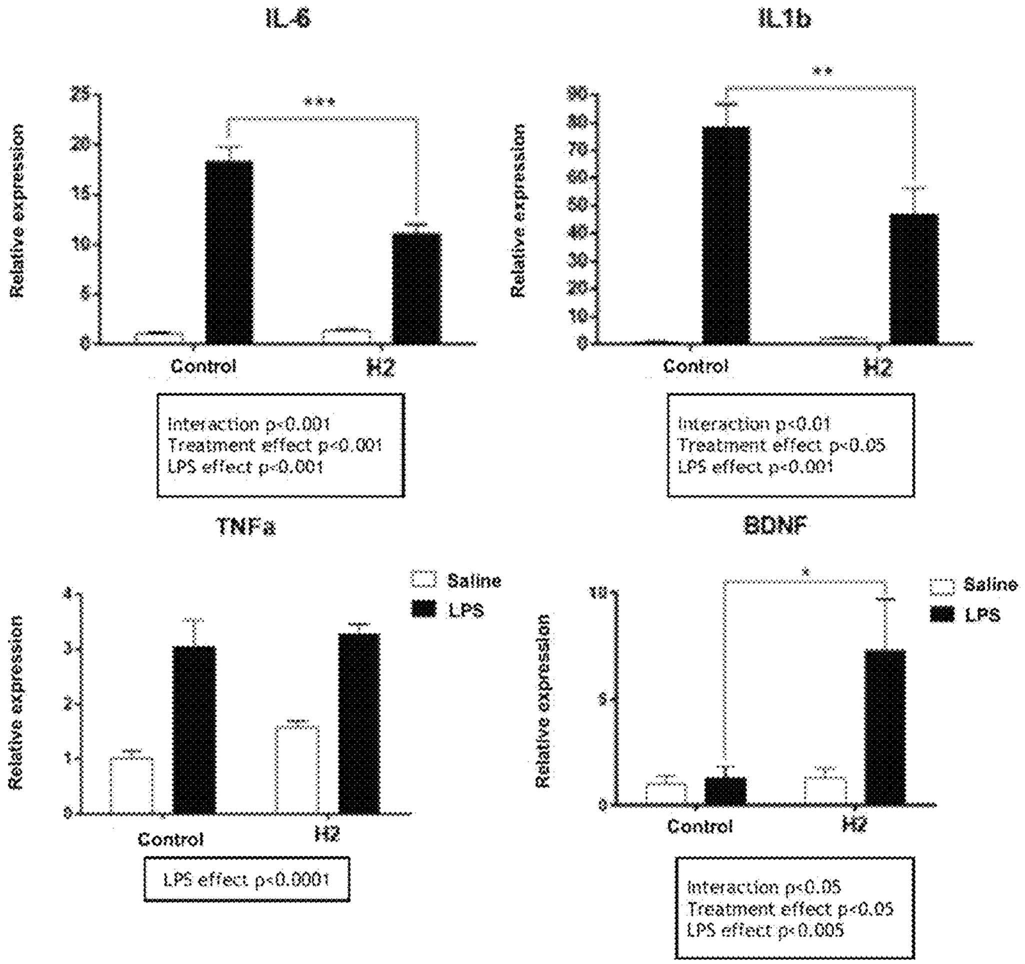
FIG. 2: In vitro effect of H2 hydrolysate on the expression of pro-inflammatory cytokines IL-6, IL-1β and TNF-α and neurotrophic factor BDNF in BV2 microglial cells co-cultured with HT22 neuronal cells treated for 6 h with LPS (n=11; *p<0.05, p<0.01, *p<0.001).

The results show that LPS induces the expression of the pro-inflammatory cytokines IL-6, IL-1β and TNF-α. H2 hydrolysate significantly decreases LPS-induced IL-6 and IL-1β expression 6 h post-treatment (FIG. 2).

2.3. Effect of H2 Hydrolysate on Neuroprotection of BV2 Microglial Cells

The H2 protein hydrolysate of the invention was tested for its ability to promote neuroprotection in microglial cells in a BV2-HT22 co-culture system (described in Example 1.1), in particular via an increase in the expression of the BDNF (Brain-Derived Neurotrophic Factor) gene, a growth factor involved in neuronal communication and homeostasis, according to the protocol described in Example 1.4.5.

The results show no effect of LPS on BDNF expression at 6 h. In contrast, treatment with H2 hydrolysate induces its expression under inflammatory conditions (FIG. 2). H2 hydrolysate supplementation facilitates the establishment of neuroprotection in inflammatory conditions.

Taken together, the various data obtained on the expression of pro-inflammatory cytokines and neurotrophic markers show that the hydrolysate of the invention possesses anti-inflammatory and neuroprotective activities.

2.4. Effect of H2 Hydrolysate on Neuroprotection of HT22 Neuronal Cells

The H2 protein hydrolysate of the invention was tested for its ability to promote neuroprotection in neuronal cells (HT22 cells) in a BV2-HT22 co-culture system (described in Example 1.1). In addition to BDNF expression, the expression of the Nerve Growth Factor (NGF) gene was also investigated using the protocol described in Example 1.4.5.

Figure 3:
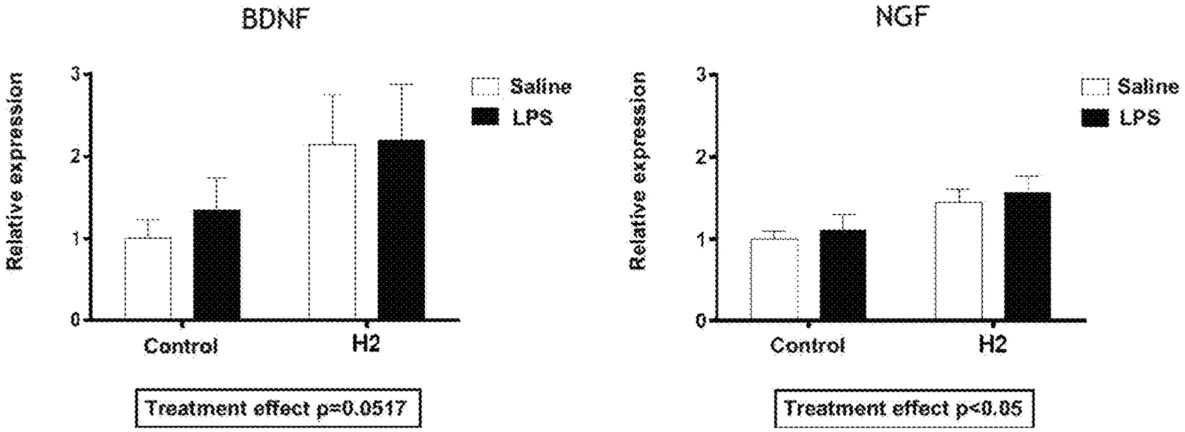
FIG. 3: In vitro effect of H2 hydrolysate on the expression of neurotrophic factors BDNF and NGF in HT22 neuronal cells co-cultured with BV2 microglial cells treated for 6 h with LPS (n=11).

The results show that LPS has no effect on the expression of BNDF and NGF but that treatment with the H2 hydrolysate increases their expression in both control (saline) and inflammatory (LPS) conditions, suggesting that the hydrolysate of the invention has neuroprotective activity (FIG. 3).

Example 3: In Vivo Effect of the Hydrolysate

For these in vivo tests, the animals were reared, fed and divided into different groups according to the protocol described in Example 1.2.

3.1. Effect of H2 Hydrolysate on Anxiety-Like Behaviour

The stress response involves the hypothalamic-pituitary-adrenal axis (HPA axis). In the presence of stress, the brain secretes cortisol in humans and corticosterone in mice, stress hormones that influence the immune system and allow a return to homeostasis. Once this return to homeostasis has been achieved, cortisol acts by negative feedback on the brain to reduce its own secretion.

In people suffering from anxiety, which accounts for 10% of the elderly, this axis is disrupted, leading to damage to the brain, particularly the hippocampus.

The effects of protein hydrolysate supplementation according to the invention on anxiety-like behaviour were studied by means of the so-called open-field (OF) test. The protocol of this test is described in Example 1.3.2.

The results in FIG. 4 represent the time spent in the centre of the OF. As expected, older animals spend less time in the centre of the device than younger animals, reflecting anxiety-like behaviour. However, older animals given H2 hydrolysate did not have a significantly different exploration time in the centre of the test than younger animals supplemented or not. H2 supplementation therefore prevents anxiety-like behaviour in older animals and maintains a level similar to that of younger animals.

The results of this test were combined with the basal corticosterone assay (according to the protocol described in Example 1.4.1). It can be seen (FIG. 4) that in the control population, older animals have higher corticosterone levels than younger animals. In the hydrolysate-supplemented population, corticosterone levels were found to be equivalent in young and old animals.

Thus, in aged animals, hydrolysate supplementation allows a return of corticosterone levels to basal levels.

3.2. Effect of H2 Hydrolysate on Stress Reactivity

It is well known that older people have impaired coping skills and difficulties in dealing with the minor stresses of everyday life. The effects of hydrolysate supplementation on stress reactivity were tested.

For this purpose, moderate stress was induced in mice by a 30-minute restraint. The protocol of this test is described in Example 1.3.6. Blood was then collected at 30, 60 and 90 minutes to determine the kinetics of corticosterone expression in response to stress (as described in Example 1.4.1).

Figure 5:
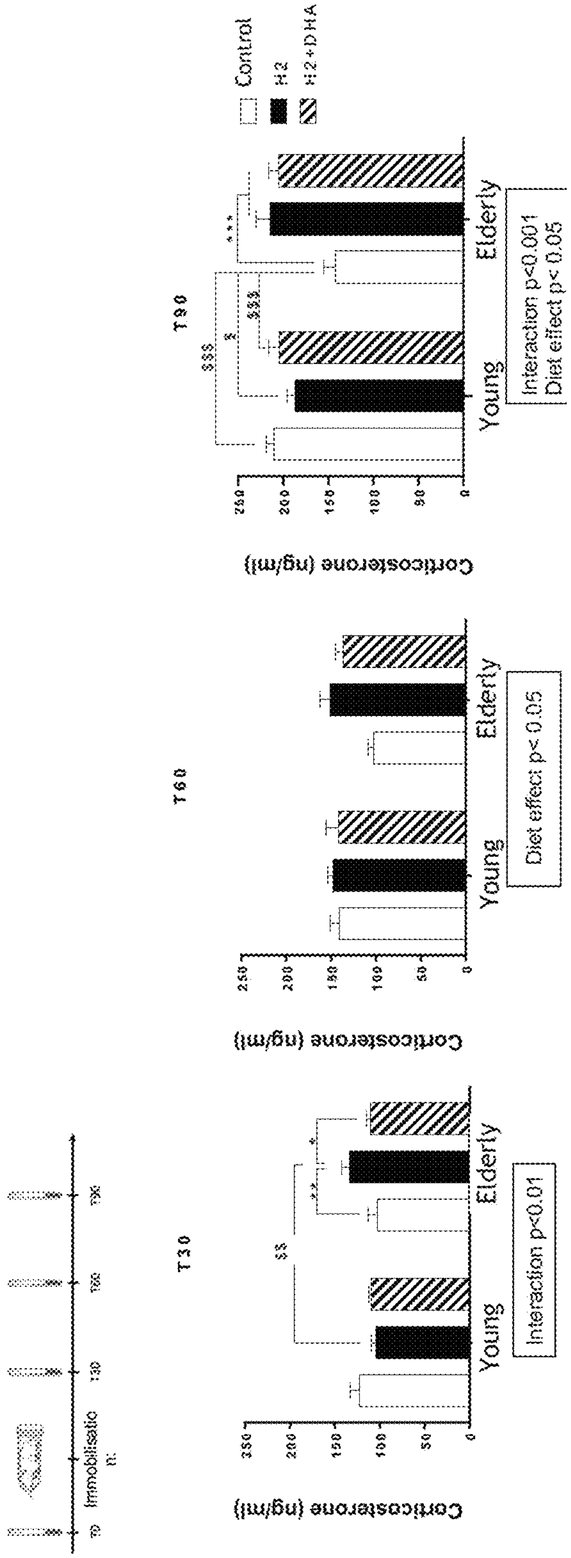
FIG. 5: Effect of H2 hydrolysate supplementation, with or without added DHA, on stress reactivity in young and old mice (n=11-13 per group; $p<0.05, $$p<0.01, $$$p<0.001 Young vs Old; *p<0.05, p<0.01, *p<0.001 Treatment vs Treatment).

The results in FIG. 5 show that at 30 min there is no age or supplementation effect, but a significant [age×supplementation] interaction was found. Indeed, at 30 min, aged control mice secrete less corticosterone after stress than aged mice supplemented with hydrolysate, suggesting an altered stress response. At 90 min, a significant [age×supplementation] interaction was found. Indeed, at 90 min, elderly control mice secrete less corticosterone after restraint stress compared to young control mice, suggesting an altered stress response. Furthermore, hydrolysate supplementation restores corticosterone levels in aged mice similar to those in young mice and prevents this age-related alteration in stress response. Furthermore, the same results were observed when the animals were supplemented with a combination of hydrolysate and DHA (FIG. 5).

Thus, supplementation of hydrolysate, with or without DHA, in aged animals restores a stress reactivity similar to that of young mice.

Figure 6:
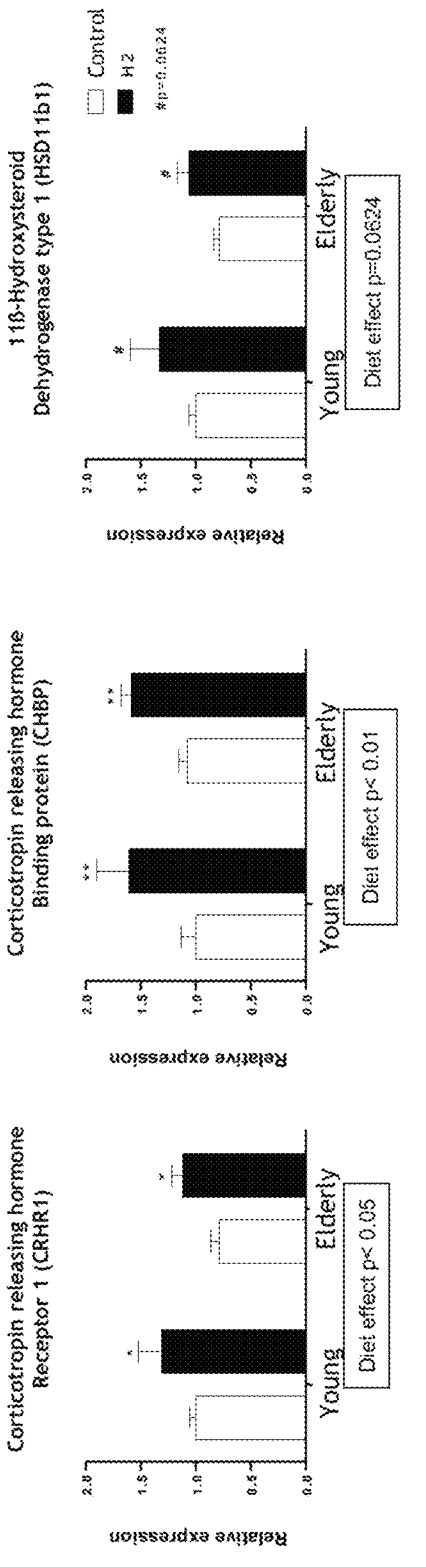
FIG. 6: Effect of H2 hydrolysate supplementation on stress response gene expression in the hypothalamus of young and old mice supplemented for 11 weeks (n=7-9 per group; *p<0.05, **p<0.01, #p=0.0624).

As a further step, the expression of genes involved in the stress response in the hypothalamus was quantified (following the protocol described in Example 1.4.5). FIG. 6 shows that age has no impact on the expression of the CrhR1, CRHBP and HSD11β1 genes. In contrast, hydrolysate supplementation significantly increases the expression of CrhR1 and CRHBP and tends to increase the expression of HSD11β1, suggesting that hydrolysate-supplemented mice have a greater modulation of stress response gene expression.

3.3. Effect of H2 Hydrolysate on Hippocampal Memory

Working memory and episodic memory, autobiographical memories involving a spatial notion, are the forms of memory most affected during the ageing process.

In animals, episodic memory cannot be assessed as such. It is therefore modelled by studying spatial memory.

3.3.1. Effect of H2 Hydrolysate on Hippocampal Short-Term Memory

The Y-maze test (described in Example 1.3.1) assesses short-term spatial working memory and involves the hippocampal-prefrontal pathway.

Figure 7:
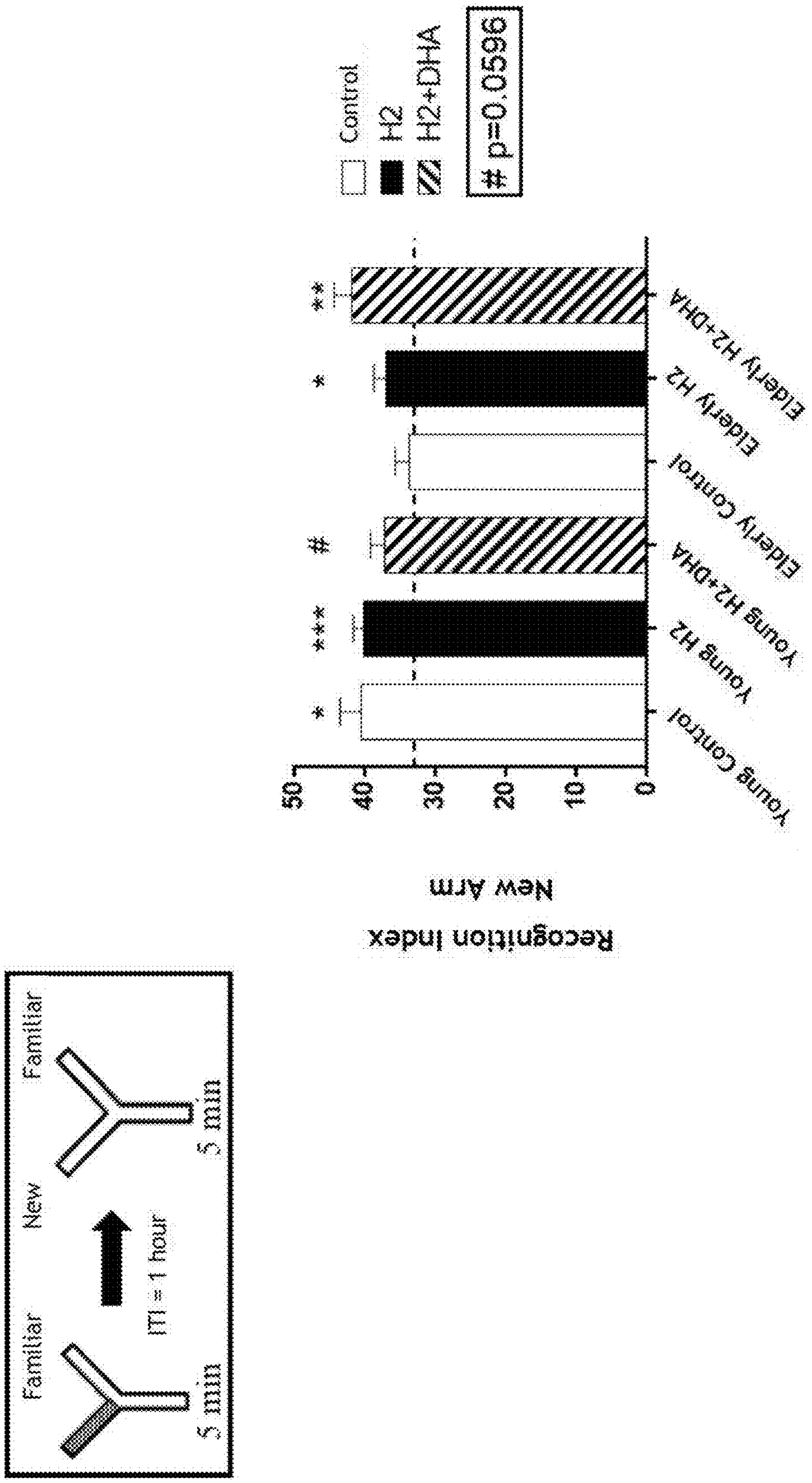
FIG. 7: Effect of H2 hydrolysate supplementation, with or without added DHA, on hippocampal short-term memory as assessed by the novel arm recognition index measure in the Y-maze test (n=11-13 per group; *p<0.05, p<0.01, *p<0.001, #p=0.0596 vs Chance (33%)).

The results shown in FIG. 7 represent the recognition index of the new arm.

The results show that young mice recognise the novel arm regardless of supplementation, as they preferentially explore this arm in a significantly different way than by chance (33%). Aged control animals show impaired memory capacity as they do not explore the novel arm in a different way to random exploration. H2 hydrolysate supplementation significantly maintains the memory capacity of aged animals (FIG. 7).

The same results were observed when the animals were supplemented with DHA-supplemented hydrolysate (FIG. 7).

Thus, supplementation with hydrolysate, with or without DHA, in aged animals prevents hippocampal dependent memory deficits.

3.3.2. Effect of H2 Hydrolysate on Hippocampal Long-Term Memory

Figure 8:
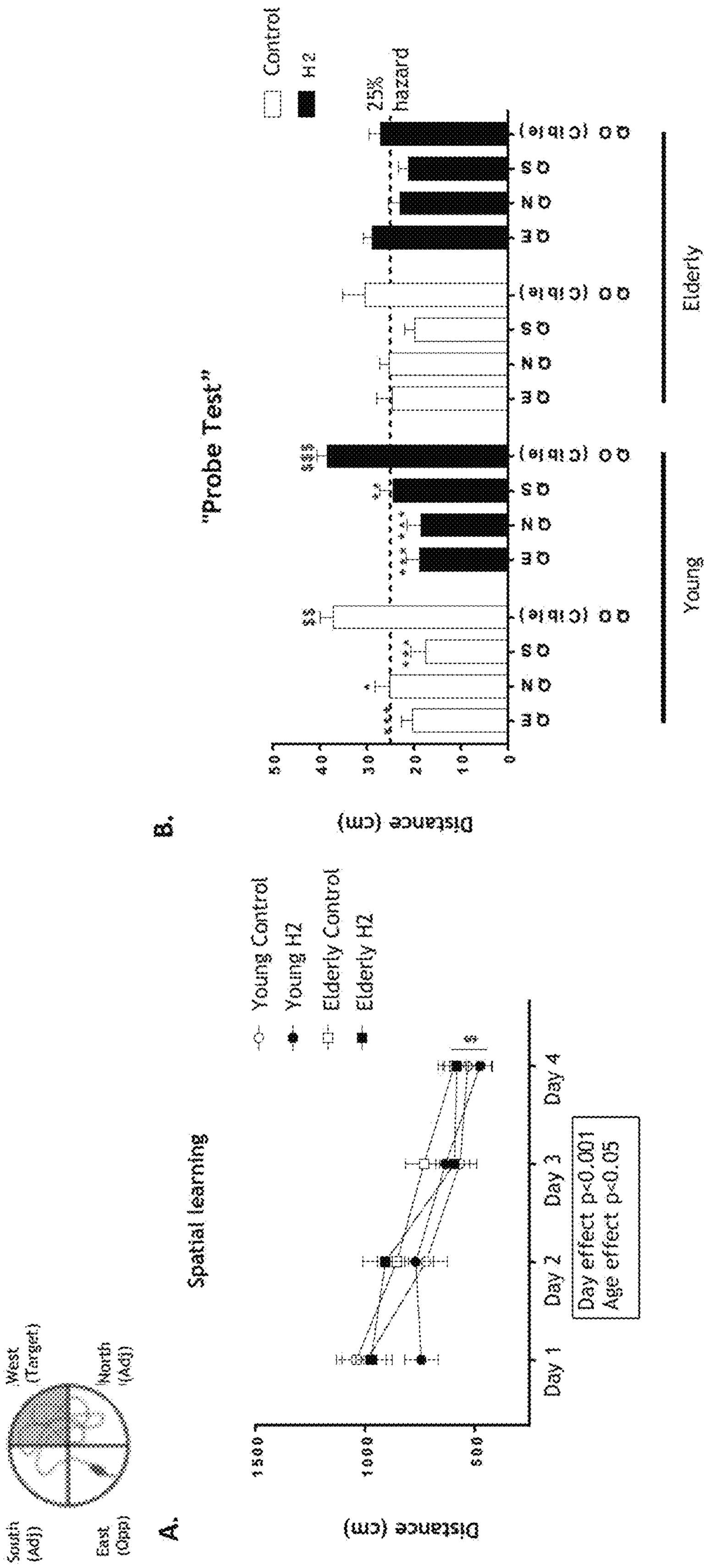
FIG. 8: Effect of H2 hydrolysate supplementation on spatial learning and long-term hippocampal memory. (A) Distance travelled to reach the platform during the 4 days of spatial learning ($p<0.05). (B) Percentage of distance travelled in the quadrants during the standard probe test ($$p<0.01; $$$p<0.001 vs Chance (25%); *p<0.05, p<0.01; *p<0.001 vs QO (target)), (n=11-13 per group).

The Morris Water Maze test (described in Example 1.3.3) assesses both learning and memory. Regarding spatial learning, all mice, young and old, supplemented and unsupplemented, learned the location of the platform since the distance travelled to reach the platform decreased over the days of learning. However, the older mice travelled further to reach the platform, indicating a spatial learning deficit (FIG. 8).

The probe test (described in Example 1.3.4) tests the animals' spatial reference memory. It was conducted 72 hours after the last day of learning.

In this test, four quadrants are distinguished, the opposite quadrant (east) corresponds to the point of introduction of the mice into the pool, the adjacent quadrants (north and south), and the target quadrant (west) which corresponds to the previous location of the now-absent platform.

The results show that young mice travel more distance in the target quadrant than in the other quadrants. These mice therefore remember the location of the platform. In contrast, older mice with a spatial learning disability covered the same distance in all four quadrants. It can therefore be concluded that these mice do not remember the location of the platform. In aged mice supplemented with hydrolysate, the impairment in memory capacity was not recovered (FIG. 8).

Thus, we do not observe any difference in learning between young and old animals, but the old animals show cognitive alterations regardless of the diet. However, a more detailed analysis of the learning strategies (described in Example 1.3.5) shows positive effects of the hydrolysate.

To reach the platform in the pool, the mice use spatial cues on the walls of the room. During the learning process, mice switch from non-spatial to more elaborate spatial strategies. Differences between the groups in the use of spatial strategies on a day-to-day basis were therefore investigated.

It was found that the control mice progressed to a spatial strategy as the days of learning progressed, before reaching a plateau in the young. For the supplemented groups, there was a greater use of spatial strategies from day 1, indicating a beneficial effect of the hydrolysate (results not shown).

Figure 9:
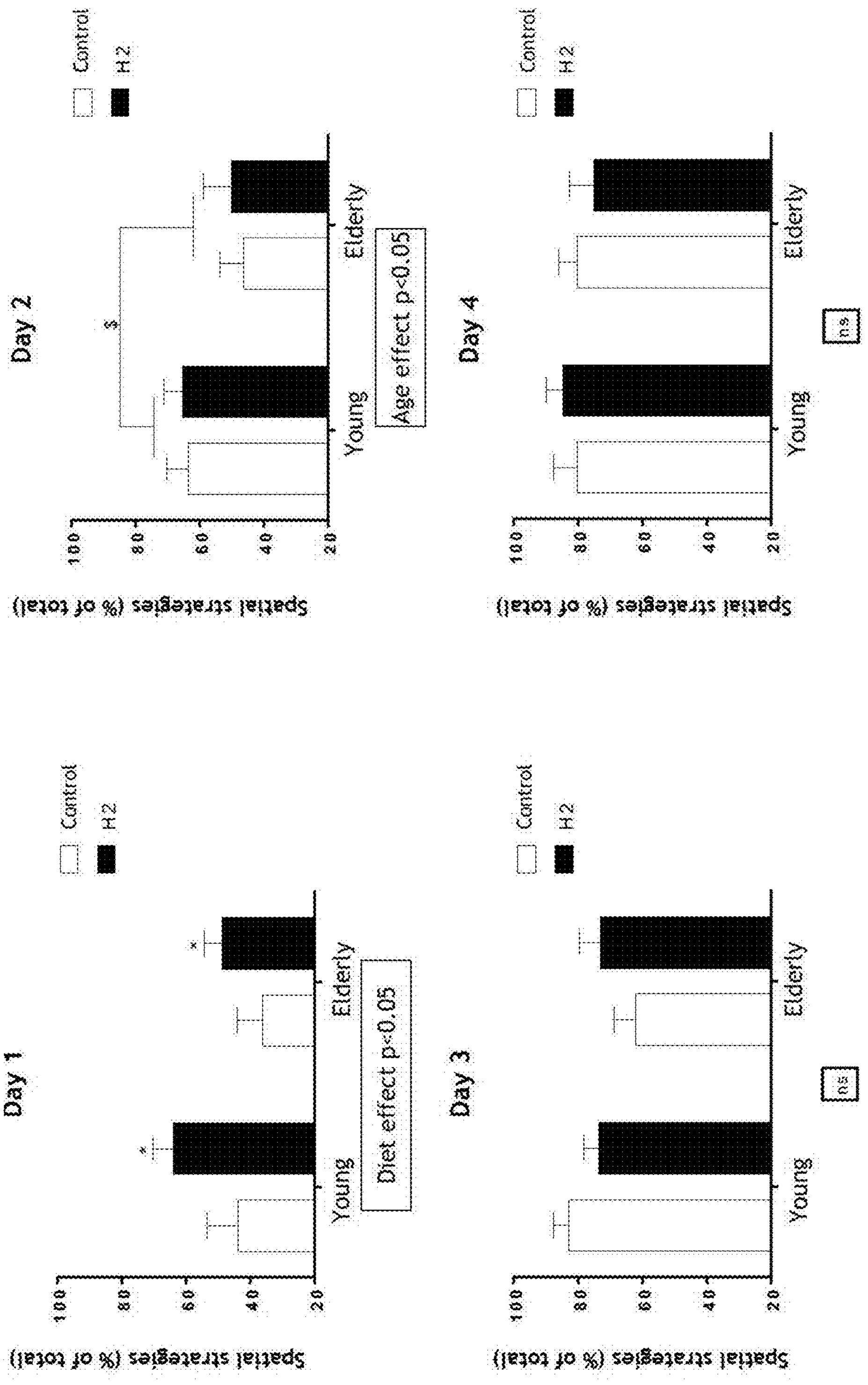
FIG. 9: Effect of H2 hydrolysate supplementation on the percentage of spatial strategies used during spatial learning in young and old mice (n=11-13 per group; diet effect *p<0.05, age effect $p<0.01).

The use of spatial strategies between the groups was also compared day by day (FIG. 9).

On day 1: mice supplemented with hydrolysate use more spatial strategies.

On day 2: The effects of hydrolysate supplementation are no longer observed, however, older mice use fewer spatial strategies than younger mice.

On days 3 and 4: The differences between the groups are no longer observed, which shows that older mice use as many spatial strategies as younger mice.

Thus, hydrolysate supplementation increases the use of spatial strategies on day 1.

In conclusion, all these in vivo tests show that hydrolysate supplementation has beneficial effects on stress reactivity on the one hand and on hippocampal-dependent short-term memory on the other.

Example 4: Biochemical Analyses of the Effects of H2 Hydrolysate on Hippocampal Neuroinflammation In physiological conditions, microglia, which are the immunocompetent cells of the brain, maintain homeostasis by monitoring the environment. These cells express CD11b. In the presence of stress or aggression, the pathogen (in this case LPS) binds to its receptor (TLR4) expressed by the microglial cells, which leads to the activation of the microglia that then express Iba1. Activation of microglia leads to activation of the NFkB pathway and thus to the production of pro-inflammatory cytokines such as IL-6, IL-1β and TNF-α. The release of these pro-inflammatory cytokines disrupts neuronal communication, which can damage surrounding neurons. The neurons then secrete neuronal growth factors (NGF, BDNF) which inhibit NFkB and thus inflammation, contributing to a return to homeostasis.

With ageing, a low-level chronic inflammation sets in. It is characterised by an increase in the number of microglia and microglial reactivity and consequently a greater release of pro-inflammatory cytokines in the basal state.

Thus, the expression of the microglial markers Cd11b and Iba1 was studied during ageing (according to the protocol described in Example 1.4.5).

Figure 10:
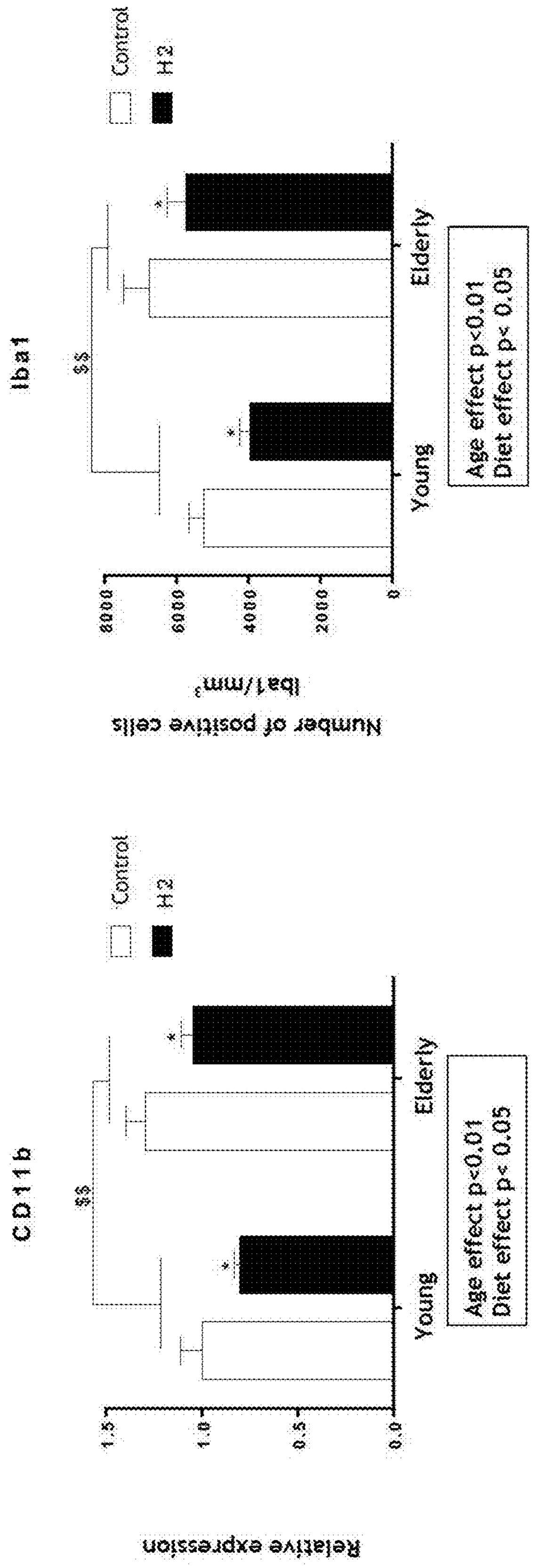
FIG. 10: Effect of H2 hydrolysate supplementation on microglial marker expression in hippocampi of mice supplemented for 11 weeks, (n=7-9 per group for CD11b and n=4 per group for Iba1; diet effect *p<0.05, age effect $$p<0.01).

The results show that aged mice express Cd11b and Iba1, markers of chronic low-grade inflammation, to a greater extent. Interestingly, hydrolysate supplementation significantly decreases their expression, thus decreasing microglial activation, which is beneficial for aged animals (FIG. 10).

In conclusion, hydrolysate supplementation has beneficial effects on hippocampal neuroinflammation.

Example 5: In Vivo Effect of H2 Hydrolysate on Hippocampal Energy Metabolism During Ageing (Chronic Inflammation)

Figure 11:
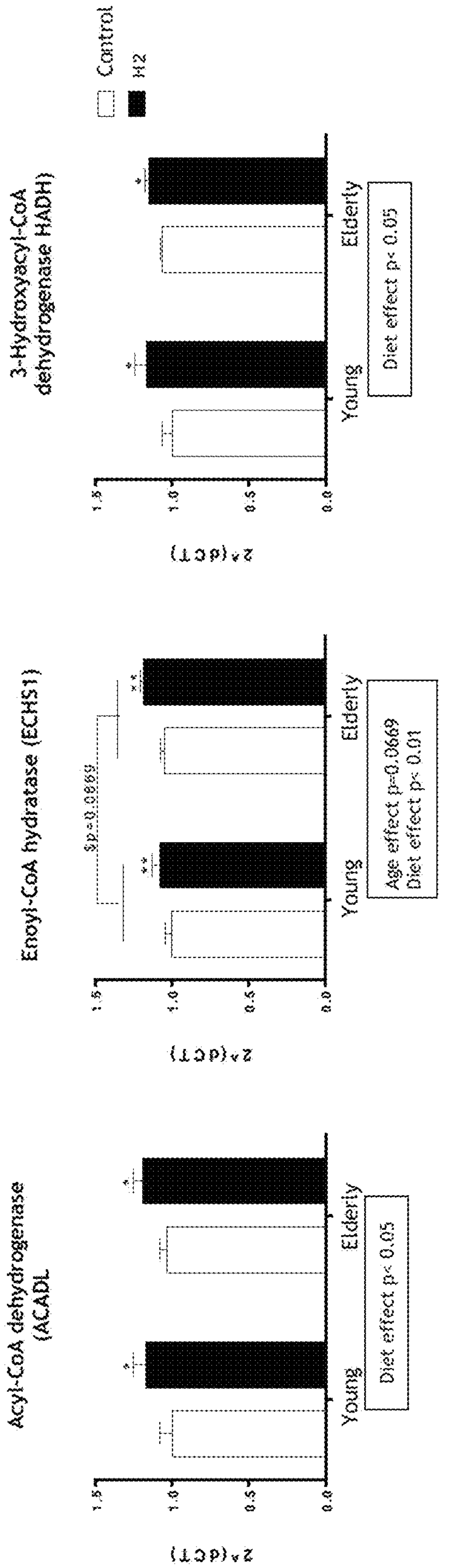
FIG. 11: Effect of H2 hydrolysate supplementation on gene expression of synthetic enzymes involved in mitochondrial and peroxisomal beta-oxidation in the hippocampus of mice supplemented for 11 weeks (n=7-8 per group; *p<0.05, p<0.01, *p<0.001).

Mitochondria and peroxisomes are organelles that play an important role in cellular energy metabolism. They are distributed at the level of the different cell types (neurons, microglia, etc.). Mitochondria are considered the "energy powerhouse" and generate ATP involved in cell maintenance and repair and necessary for certain functions such as neurotransmission in the case of neurons. By a similar mechanism to the mitochondrion, peroxisomes (cellular organelles mainly involved in cellular detoxification) also perform β-oxidation off long-chain fatty acids. The results (following the protocol described in Example 1.4.6) show that enzymes involved in mitochondrial and peroxisomal β-oxidation are impacted by hydrolysate supplementation (FIG. 11). Indeed, the expression of acyl-CoA dehydrogenase, enoyl-CoA hydratase, 3-hydroxyacyl-CoA dehydrogenase and 3-ketoacyl-CoA thiolase (involved in the $1^{st}$, $2^{nd}$, $3^{rd}$, and last step of mitochondrial β-oxidation, respectively) is increased by supplementation. An interaction between age and supplementation was found for the expression of acyl-CoA oxidase (involved in the 1st step of peroxisomal β-oxidation). Unexpectedly, the H2 hydrolysate amplified the expression of genes for enzymes involved in cell metabolism.

Example 6: In Vivo Effect of H2 Hydrolysate on Hippocampal Antioxidant Defences During Ageing (Chronic Inflammation)

Figure 12:
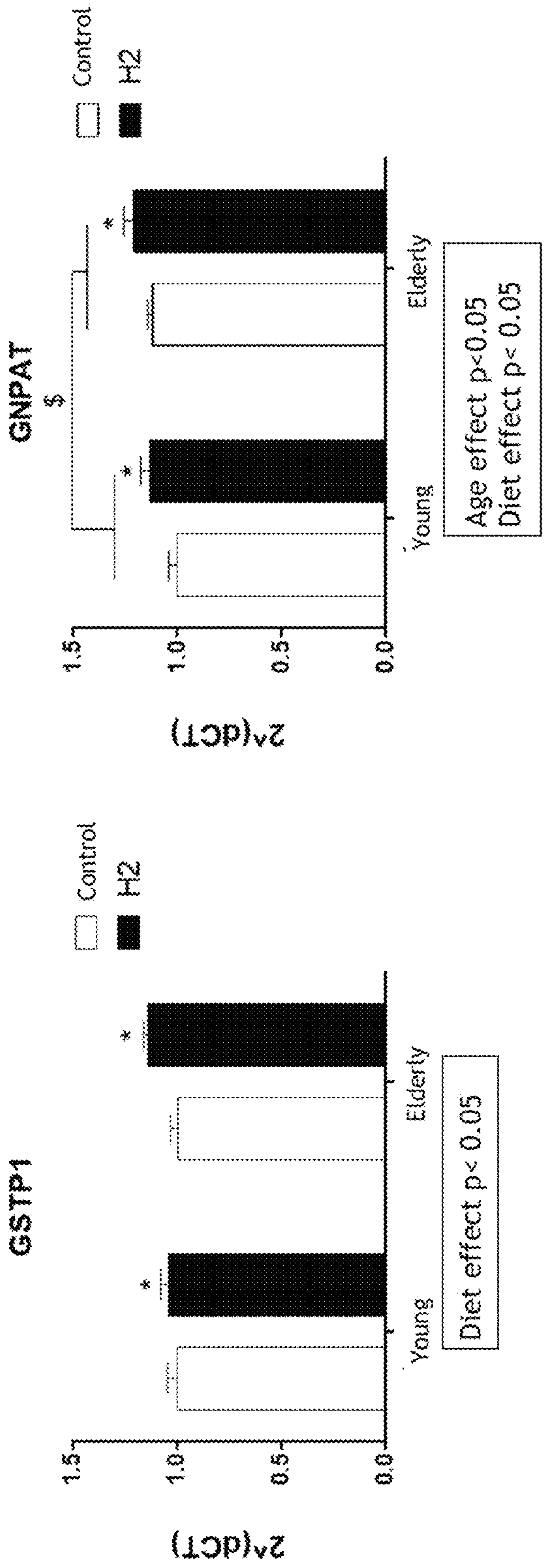
FIG. 12: Effect of H2 hydrolysate supplementation on gene expression of synthetic enzymes involved in antioxidant defence in the hippocampus of mice supplemented for 11 weeks (n=7-8 per group; diet effect *p<0.05; age effect $p<0.05).

During ageing, cells tend to accumulate dysfunctional aggregated molecules resulting from oxidative imbalance: an increase in the production of reactive oxygen species and/or a decrease in antioxidant defences is observed. We evaluated the effect of the hydrolysate on glutathione S-transferase, which is an antioxidant defence enzyme, and on glyceronephosphate O-acyltransferase, which is involved in the first stage of the synthesis of plasmalogens, lipids with an antioxidant role. The results (obtained according to the protocol described in Example 1.4.6) show that hydrolysate supplementation increases the expression of genes for these enzymes, suggesting a positive effect of the hydrolysate on antioxidant defences (FIG. 12).

Example 7: In Vivo Effect of H2 Hydrolysate on Hippocampal Neuroinflammation in Response to Acute Inflammation The effect of the hydrolysate was assessed on acute (LPS-induced) inflammation in mice supplemented for 18 days with hydrolysate or DHA (according to the protocol described in Example 1.4.5).

Figure 13:
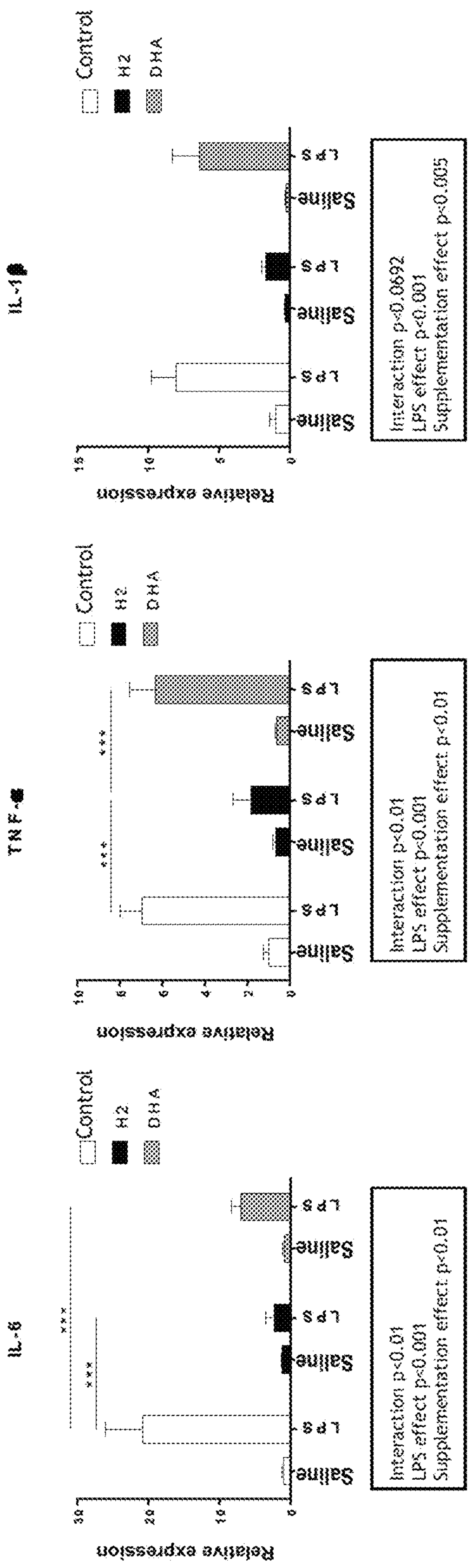
FIG. 13: Effect of 18-day supplementation with H2 hydrolysate or DHA on gene expression of pro-inflammatory cytokines in the hippocampus of mice in response to LPS (n=4-6 per group; ***p<0.001).

Changes in the expression of pro-inflammatory cytokines in response to LPS (FIG. 13) were then assessed. As expected, LPS significantly increased the expression of IL-6, TNF-α, IL-1β. Supplementation significantly modulated the expression of pro-inflammatory cytokines (IL-6, TNF-α and IL-1β). An LPS×supplementation interaction was found for IL-6 and TNF-α and a trend for IL-1β. Indeed, in LPS-treated animals, IL-6 expression was significantly decreased by hydrolysate and DHA supplementation, while TNF-α expression was decreased by hydrolysate supplementation.

Figure 14:
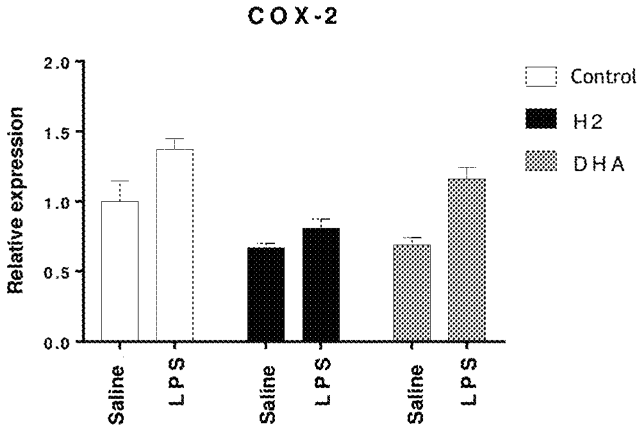
FIG. 14: Effect of 18-day supplementation with H2 hydrolysate or DHA on COX-2 gene expression in mouse hippocampus in response to LPS (n=4-6 per group).

The expression of COX-2 (according to the protocol described in Example 1.4.5), involved in the synthesis of lipid mediators of inflammation, was also determined. Its expression was significantly increased by LPS treatment and significantly decreased by supplementation (FIG. 14).

Figure 15:
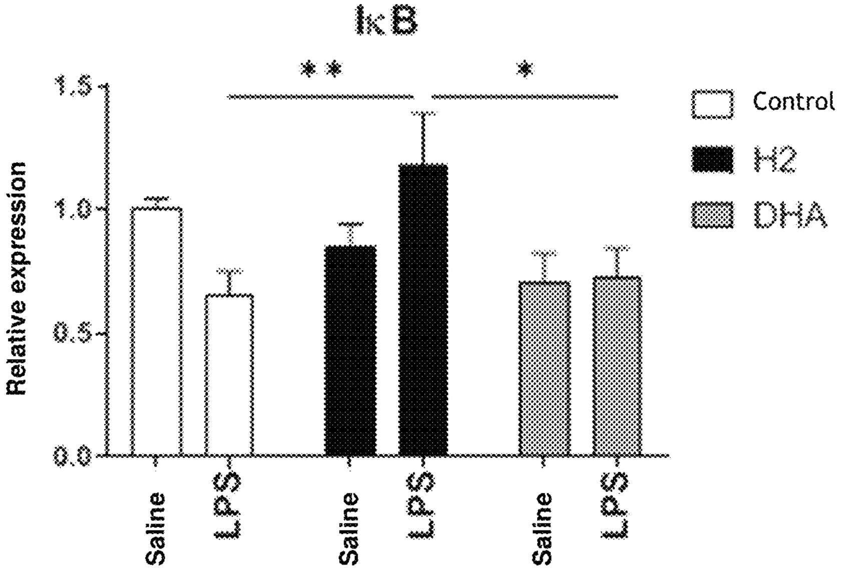
FIG. 15: Effect of 18-day supplementation with H2 hydrolysate or DHA on protein expression of IkB in mouse hippocampus in response to LPS (n=5-6 per group; *p<0.05, **p<0.01).

Protein expression of IkB (according to the protocol described in Example 1.4.7) involved in the regulation of the expression of these inflammatory factors was assessed (FIG. 15). The supplements have a significant effect on the expression of IkB (which is an inhibitor of NFkB, itself responsible for the synthesis of inflammatory factors) and an interaction between the supplements and LPS has been demonstrated. Indeed, under inflammatory conditions, IkB expression is significantly increased by hydrolysate supplementation.

PUFAs can be converted into bioactive lipid derivatives, or oxylipins, which contribute to their immunomodulatory properties. Derivatives of n-6 PUFAs are mostly pro-inflammatory while those derived from n-3 PUFAs are anti-inflammatory. The impact of supplementation on fatty acid composition (according to the protocol described in Example 1.4.8) and on the concentration of n-6 and n-3 PUFA-derived oxylipins in the hippocampus (according to the protocol described in Example 1.4.9) after treatment with NaCl or LPS was assessed.

Firstly, it has been shown that supplementation has an impact on PUFA composition in the cortex: supplementation increases n-3 PUFA levels and decreases n-6 PUFA levels. Almost all PUFAs are affected: 20:3 n-6, 20:4 n-6, 22:4 n-6, 22:5 n-6, 20:5 n-3 and 22:6 n-3. Supplementation modulates the concentrations of arachidonic acid derivatives and DHA (FIG. 16). In addition, an interaction between LPS factors and supplementation was found for arachidonic acid-derived and DHA-derived oxylipins. Indeed, for n-6 PUFA derivatives, under saline conditions, hydrolysate supplementation increased the concentration of α-PGF2 compared to the control group. In LPS-treated animals, hydrolysate supplementation increased the concentration of PGE2 ($p<0.01$), PGD2 ($p<0.01$), PGA1 ($p<0.001$), 15-HETE ($p<0.001$), 8-HETE ($p<0.001$), 12-HETE ($p<0.001$), 5-oxoETE ($p<0.001$) compared to saline treated animals. It also increased levels of PGA1, LxA4, 15-HETE, 8-HETE, 5-oxoETE compared to controls (LxA4 and 8-HETE: $p<0.05$, 5-oxoETE: $p<0.01$) or DHA supplemented animals (LxA4 and 8-HETE: $p<0.05$, 15-HETE: $p<0.01$, PGA1: $p<0.001$). Regarding DHA derivatives, under inflammatory conditions, hydrolysate supplementation increased the levels of 14-HDoHE ($p<0.001$), 17-HDoHE ($p<0.001$) and 7-MaR1 ($p<0.01$) compared to NaCl-treated animals and to control animals (14-HDoHE: $p<0.05$) or DHA supplementation (17-HDoHE: $p<0.05$, 7-MaR1: $p<0.001$).

Figure 17:
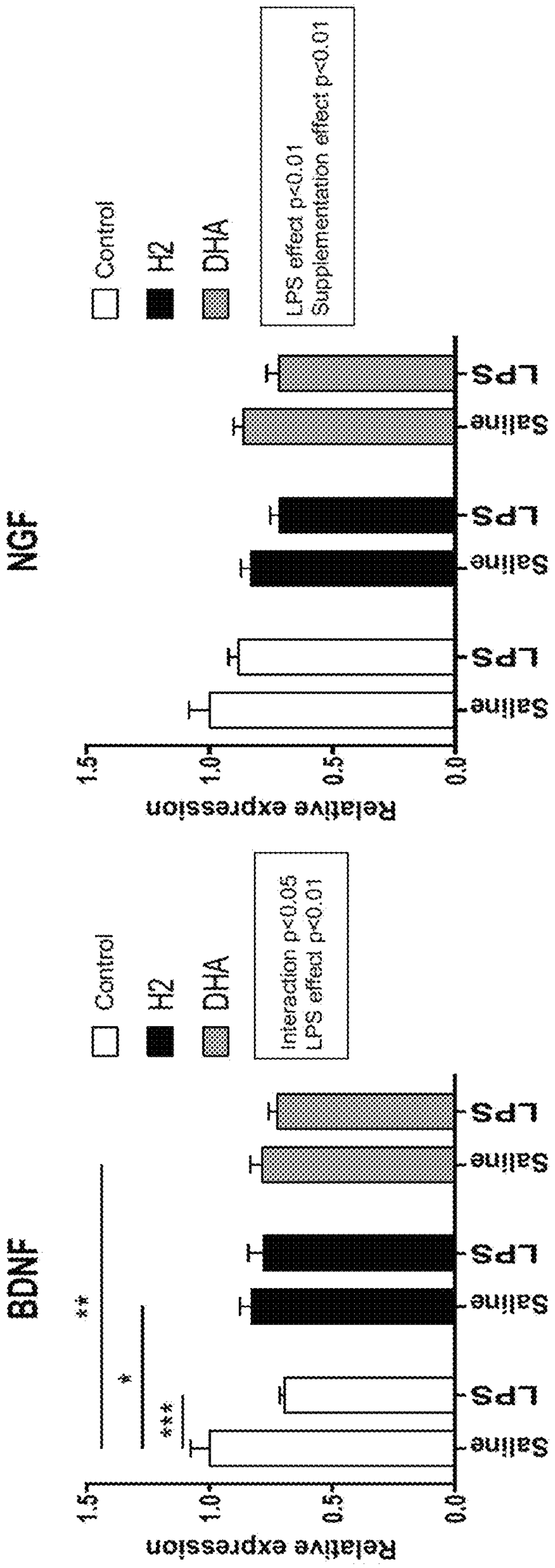
FIG. 17: Effect of 18-day supplementation with H2 hydrolysate or DHA on gene expression of BDNF and NGF neurotrophins in the mouse hippocampus in response to LPS (n=4-6 per group; *p<0.05, p<0.01, *p<0.001).

Example 8: In Vivo Effect of H2 Hydrolysate on Neuronal Survival in Response to Acute Inflammation The effect of H2 hydrolysate and DHA supplementation on the expression of the neurotrophins BDNF and NGF, according to the protocol described in Example 1.4.5, was assessed (FIG. 17). Supplementation decreased NGF expression and BDNF expression in basal conditions. In response to LPS, BDNF expression is stable in the hydrolysate and DHA supplemented groups while it decreases in the control group.

REFERENCES

1. European Commission. 2009 Ageing Report: Economic and Budgetary Projections for the EU-27 Member States (2008-2060). Brussels: European Communities, 2009.
2. Kinsella K and He. W. An aging world, International population reports 2008. National Institute On Aging, U.S. Census Bureau, p 1-191.
3. VAB Nutrition. Thematic focus: current and emerging health issues that affect or will affect the “Seniors” target and the nutritional offer to be developed to delay or limit their impact. 2009. Bibliographical study financed by Valorial/CRITT Santé Bretagne.
4. Bousquet J, et al, Operational Definition of Active and Healthy Ageing (AHA): A Conceptual Framework. J Nutr Health Aging. 2015. 19(9):955-60.

5. Banfield Pet Hospital's State of Pet Health 2013 Report. available at www.banfield.com/Banfield/media/PDF/Downloads/soph/Banfield-State-of-Pet-Health-Report_2013. pdf 6. Landsberg G M, Nichol J, Araujo J A. Cognitive dysfunction syndrome: a disease of canine and feline brain aging. Vet Clin North Am Small Anim Pract. 2012. 42(4):749-68.

7. Salvin H. E., McGreevy P. D., Sachdev P. S., Valenzuela M. J. Under diagnosis of canine dysfunction: a cross sectional survey in older companion dogs. The Veterinary Journal. 2010. 184: 277-281.

8. De Smedt-Peyrusse V., Sargueil F., Moranis A., Harizi H., Mongrand S., Layé S. Docosahexaenoic acid prevents lipopolysaccharide-induced cytokine production in microglial cells by inhibiting lipopolysaccharide receptor presentation but not its membrane subdomain localization. J Neurochem 2008. 105:296-307.

9. Rey C., Delpech J. C., Madore C., Nadjar A., Greenhalgh AD., Amadieu C., Aubert A., Pallet V., Vaysse C., Layé S., Joffre C. Dietary n-3 long chain PUFA supplementation promotes a pro-resolving oxylipin profile in the brain. Brain Behav Immun 2019. 76:17-27.

10. Mingam R, Moranis A., Bluthé R M., De Smedt-Peyrusse V., Kelley KW., Guesnet P., Lavialle M., Dantzer R., Layé S. Uncoupling of interleukin-6 from its signalling pathway by dietary n-3-polyunsaturated fatty acid deprivation alters sickness behaviour in mice. Eur J Neurosci 2008 28:1877-86. 11. Labrousse V F, Nadjar A, Joffre C, Costes L, Aubert A, Gregoire S, Bretillon L, Laye S. Short-term long chain omega3 diet protects from neuroinflammatory processes and memory impairment in aged mice. PLoS One 2012. 7:e36861.

12. Moranis A., Delpech JC., De Smedt-Peyrusse V., Aubert A., Guesnet P., Lavialle M., Joffre C., Laye S. Long term adequate n-3 polyunsaturated fatty acid diet protects from depressive-like behavior but not from working memory disruption and brain cytokine expression in aged mice. Brain Behav Immun 2012. 26:721-31.

13. Morris R. Developments of a water-maze procedure for studying spatial learning in the rat. Journal of Neuroscience Methods 1984. 11:47-60.

14. Bensalem J., Dudonné S., Gaudout D., Servat L., Calon F., Desjardins Y., Layé S., Lafenêtre P., Pallet V. Polyphenol-rich extract from grape and blueberry attenuates cognitive decline and improves neuronal function in aged mice. J Nutr Sci 2018. 7:e19.

15. Brody D. L., Holtzman D. M. Morris water maze search strategy analysis in PDAPP mice before and after experimental traumatic brain injury. Exp Neurol 2006. 197:330-340.

16. Garthe A., Behr J., Kempermann G. Adult-Generated Hippocampal Neurons Allow the Flexible Use of Spatially Precise Learning Strategies. PLOS ONE 2009. 4:e5464.

17. Ruediger S., Spirig D., Donato F., Caroni P. Goal-oriented searching mediated by ventral hippocampus early in trial-and-error learning. Nature Neuroscience 2012. 15:1563-1571.

18. Rey C., Nadjar A., Buaud B., Vaysse C., Aubert A., Pallet V., Layé S., Joffre C. Resolvin D1 and E1 promote resolution of inflammation in microglial cells in vitro. Brain Behav. Immun. 2016. 55:249-259.

19. Folch J., Lees M., Sloane Stanley GH. A simple method for the isolation and purification of total lipids from animal tissues. J. Biol. Chem. 1957. 226: 497-509.20. Le Faouder P., Baillif V., Spreadbury I., Motta J. P., Rousset P., Chene G., Guigne C., Terce F., Vanner S., Vergnolle N., Bertrand-Michel J., Dubourdeau M., Cenac N. LC-MS/MS method for rapid and concomitant quantification of pro-inflammatory and pro-resolving polyunsaturated fatty acid metabolites. J. Chromatogr. B Analyt. Technol. Biomed. Life Sci. 2013. 932:123-133.

21. Adler-Nissen J. Enzymatic hydrolysis of proteins for increased solubility. J. Agric. Food Chem. 1976 24:1090-1093.

22. Nielsen, P. M.; Petersen, D.; Dambmann, C. Improved method for determining food protein degree of hydrolysis. Journal of Food Science 2001, 66, 642-646.

23. Mathieu-Resuge, et al, Trophic ecology of suspension-feeding bivalves inhabiting a north-eastern Pacific coastal lagoon: Comparison of different biomarkers. Marine environmental research, 145, 155-16 (2019).

24. F. Guérard et al, Journal of Molecular Catalysis B: Enzymatic 19-20 (2002) 489-498.

The invention claimed is:

1. A protein hydrolysate obtained from at least one protein source from bluefish comprising:

(I) a degree of hydrolysis (DH) of at least 10% to less than 20%, as determined by a pH-stat method, (II) at least 80% to less than 91.75% of water-soluble proteins with a molecular weight of less than 1000 Da, (III) at least 0.3% to no more than 3% of phospholipids, and (IV) at least 0.5% to a maximum of 5% of DHA and EPA, wherein the phospholipids and EPA are endogenously derived from the at least one protein source from the bluefish.

2. The protein hydrolysate according to claim 1, wherein said protein source is at least derived from bluefish heads.

3. The protein hydrolysate according to 1, wherein said protein hydrolysate is supplemented with docosahexaenoic acid (DHA).

4. The protein hydrolysate according to claim 1, wherein the protein hydrolysate is obtained by an enzymatic hydrolysis process comprising the steps of:

(a) providing a protein source;

(b) grinding said protein source;

(c) optionally, adjusting the pH;

(d) adding at least one hydrolysing enzyme;

(e) heating;

(f) separation; and (g) drying.

5. A food composition comprising at least one protein hydrolysate as defined in claim 1, wherein the food composition is a complete food or a food supplement.

6. The food composition according to claim 5, wherein said food composition is a functional food or nutraceutical.

7. The food composition according to claim 6, wherein said food composition is a food supplement.

8. The food composition according to claim 7, wherein said food supplement is a functional food or nutraceutical for humans.

9. The food composition according to claim 5, wherein said food composition is a pet food.

10. The food composition according to claim 9, wherein said pet food is a dog or cat food.

11. A method of preparing a protein hydrolysate as defined in claim 1, comprising the steps of:

(a) providing a protein source;

(b) grinding said protein source;

(c) optionally, adjusting the pH;

(d) adding at least one hydrolysing enzyme;

(e) heating;

(f) separation; and (g) drying.

12. The method for the preparing a protein hydrolysate according to claim 11, further comprising a DHA supplementation step.

13. A kit comprising, in a single package, a plurality of containers:

a) at least one protein hydrolysate as defined in claim 1;

b) one or more pet food ingredients, preferably selected from the group consisting of proteins, peptides, amino acids, cereals, carbohydrates, fats or lipids, nutrients, palatability enhancers, animal digestates, meat meal, gluten, preservatives, surfactants, texturing, stabilising or colouring agents, inorganic phosphate compounds, flavourings and/or seasoning;

c) optionally at least DHA.

14. A pharmaceutical composition comprising at least one protein hydrolysate as defined claim 1, a pharmaceutically acceptable carrier and/or an excipient.

15. The pharmaceutical composition as defined in claim 14, for use as a medicinal product.

16. The protein hydrolysate as defined in claim 1, for use as a medicinal product.

* * * * *